(12) United States Patent
Tamiaki et al.

(10) Patent No.: US 8,633,022 B2
(45) Date of Patent: Jan. 21, 2014

(54) DUAL-TERMINAL AMIDE HYDROGELLING AGENT

(75) Inventors: Hitoshi Tamiaki, Kusatsu (JP); Keishiro Ogawa, Kusatsu (JP); Kazunori Toma, Tokyo (JP)

(73) Assignees: The Ritsumeikan Trust, Kyoto (JP); Asahi Kasei Kabushiki Kaisha, Osaka (JP)

( * ) Notice: Subject to any disclaimer, the term of this patent is extended or adjusted under 35 U.S.C. 154(b) by 168 days.

(21) Appl. No.: 13/201,111

(22) PCT Filed: Feb. 23, 2010

(86) PCT No.: PCT/JP2010/052764
§ 371 (c)(1),
(2), (4) Date: Aug. 11, 2011

(87) PCT Pub. No.: WO2010/098320
PCT Pub. Date: Sep. 2, 2010

(65) Prior Publication Data
US 2011/0312092 A1     Dec. 22, 2011

(30) Foreign Application Priority Data
Feb. 24, 2009   (JP) ................................. 2009-040398

(51) Int. Cl.
*C12N 5/00* (2006.01)
*C07C 239/00* (2006.01)

(52) U.S. Cl.
USPC ............................ 435/374; 435/373; 435/395

(58) Field of Classification Search
USPC ............................ 435/373, 374, 395; 564/158
See application file for complete search history.

(56) References Cited

FOREIGN PATENT DOCUMENTS

| | | |
|---|---|---|
| JP | 6-141851 A | 5/1994 |
| JP | 2001-122889 A | 5/2001 |
| JP | 2004-262809 A | 9/2004 |
| JP | 2005-232061 A | 9/2005 |
| JP | 2005-232278 A | 9/2005 |
| JP | 2007-217551 A | 8/2007 |
| JP | 2009-84272 A | 4/2009 |

OTHER PUBLICATIONS

English translation of JP 2007217551 downloaded from the JPO Mar. 14, 2013.*

Estroff et al., "Water Gelation by Small Organic Molecules", Chemical Reviews, American Chemical Society, vol. 104, No. 3, Mar. 2004, pp. 1201-1217.
International Search Report, dated Apr. 13, 2010 in PCT/JP2010/052764.
Lutolf et al., "Designing materials to direct stem-cell fate", Nature, vol. 462, Nov. 26, 2009, pp. 433-441.
Stebani et al., "Liquid crystalline derivatives of oligoethyleneamines and -amino ethers with amide, ester,.urea or urethane functions", Journal of Materials Chemistry, vol. 7, No. 4, 1997, pp. 607-614.
Terech et al., "Low Molecular Mass Gelators of Organic Liquids and the Properties of Their Gels" Chemical Reviews, American Chemical Society, vol. 97, No. 8, Dec. 1997, pp. 3133-3159.
van Esch at al., "New Functional Materials Based on Self-Assembling Organogels: From Serendipity towards.Design", Angew. Chem. Int. Ed., vol. 39, No. 13, Jul. 3, 2000, pp. 2263-2266.

* cited by examiner

*Primary Examiner* — Susan Hanley
(74) *Attorney, Agent, or Firm* — Birch, Stewart, Kolasch & Birch, LLP

(57) ABSTRACT

The invention relates to a benzamide derivative represented by formula (1):

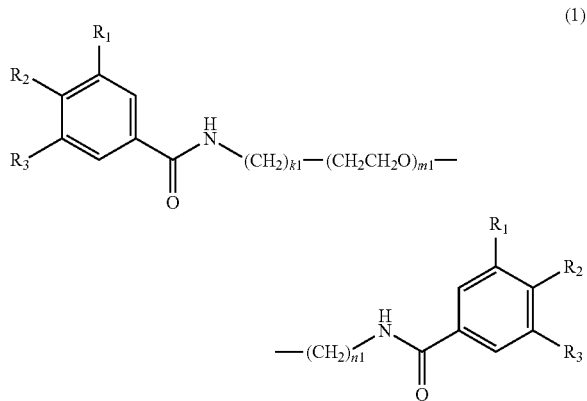

wherein k1 represents an integer from 0-4, m1 represents an integer from 1-100, and n1 represents an integer from 1-6. In addition, $R_1$ represents a hydrocarbon group with 8-22 carbon atoms bonded to an oxygen atom wherein the oxygen atom is bonded to the adjacent ring of said derivative; $R_2$ represents H or a hydrocarbon group with 1-22 carbon atoms bonded to an oxygen atom wherein the oxygen atom is bonded to the adjacent ring of said derivative; $R_3$ represents H or a hydrocarbon group with 1-22 carbon atoms bonded to an oxygen atom wherein the oxygen atom is bonded to the adjacent ring of said derivative; and $R_2$ and $R_3$ are not H at the same time.

21 Claims, 9 Drawing Sheets

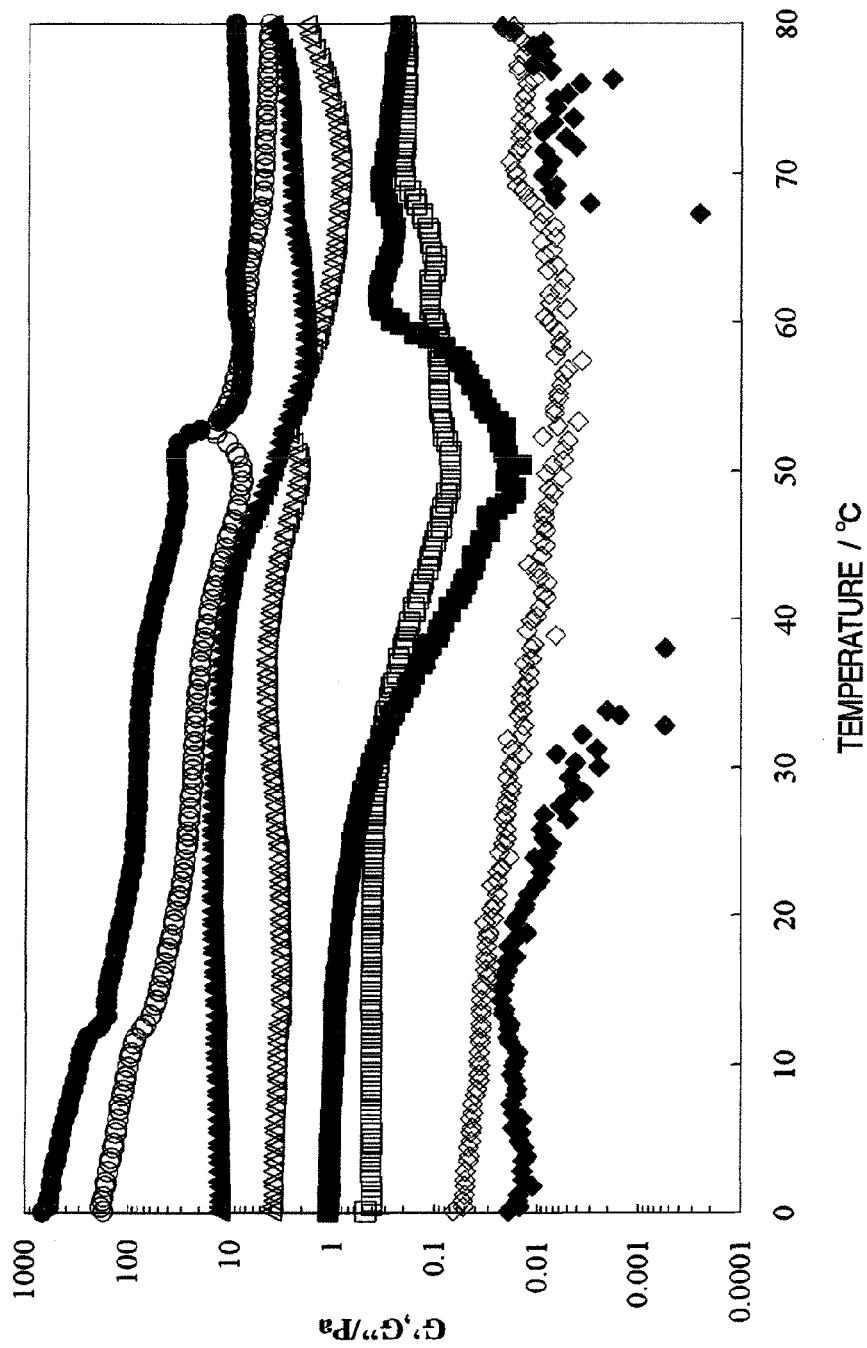

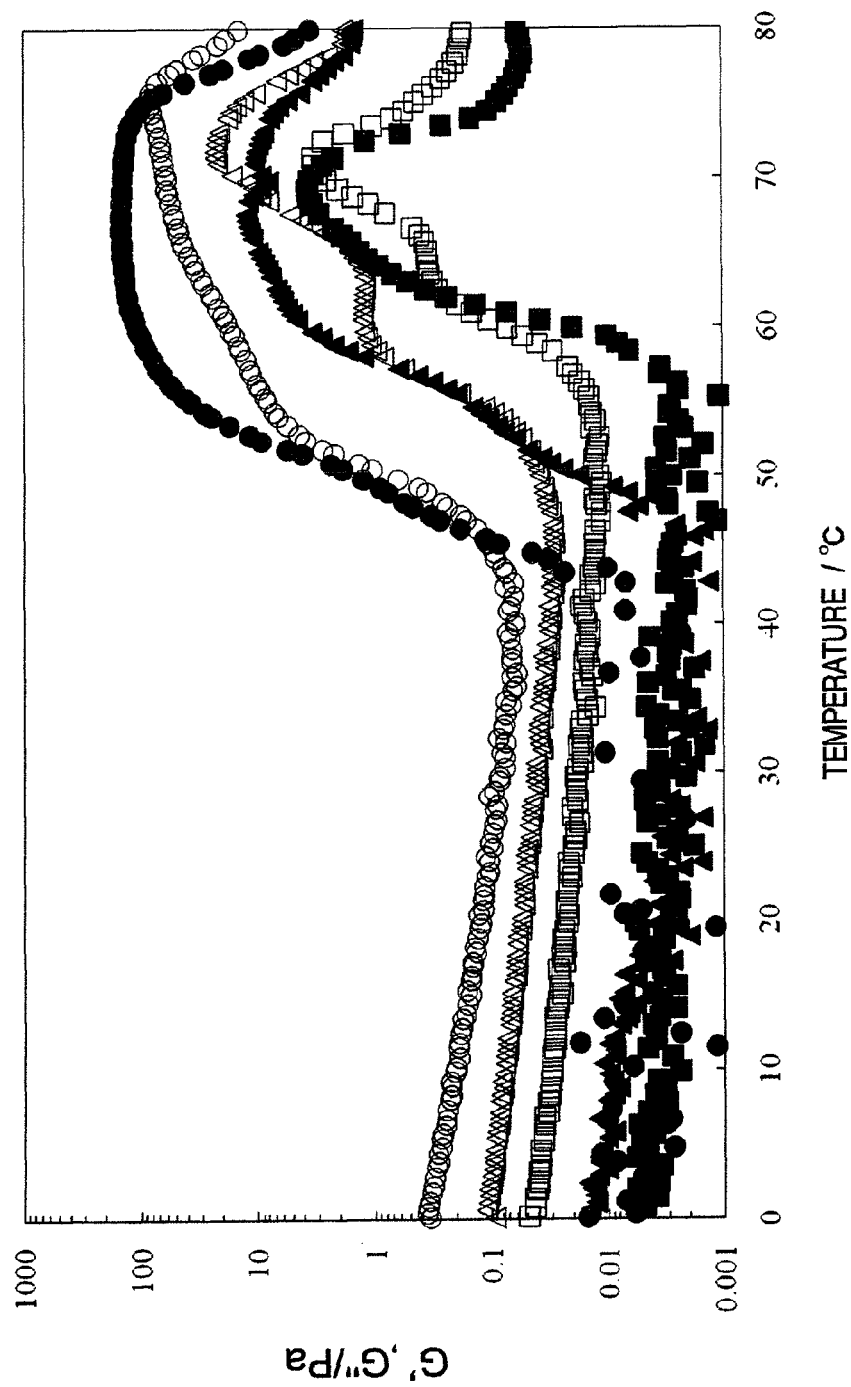

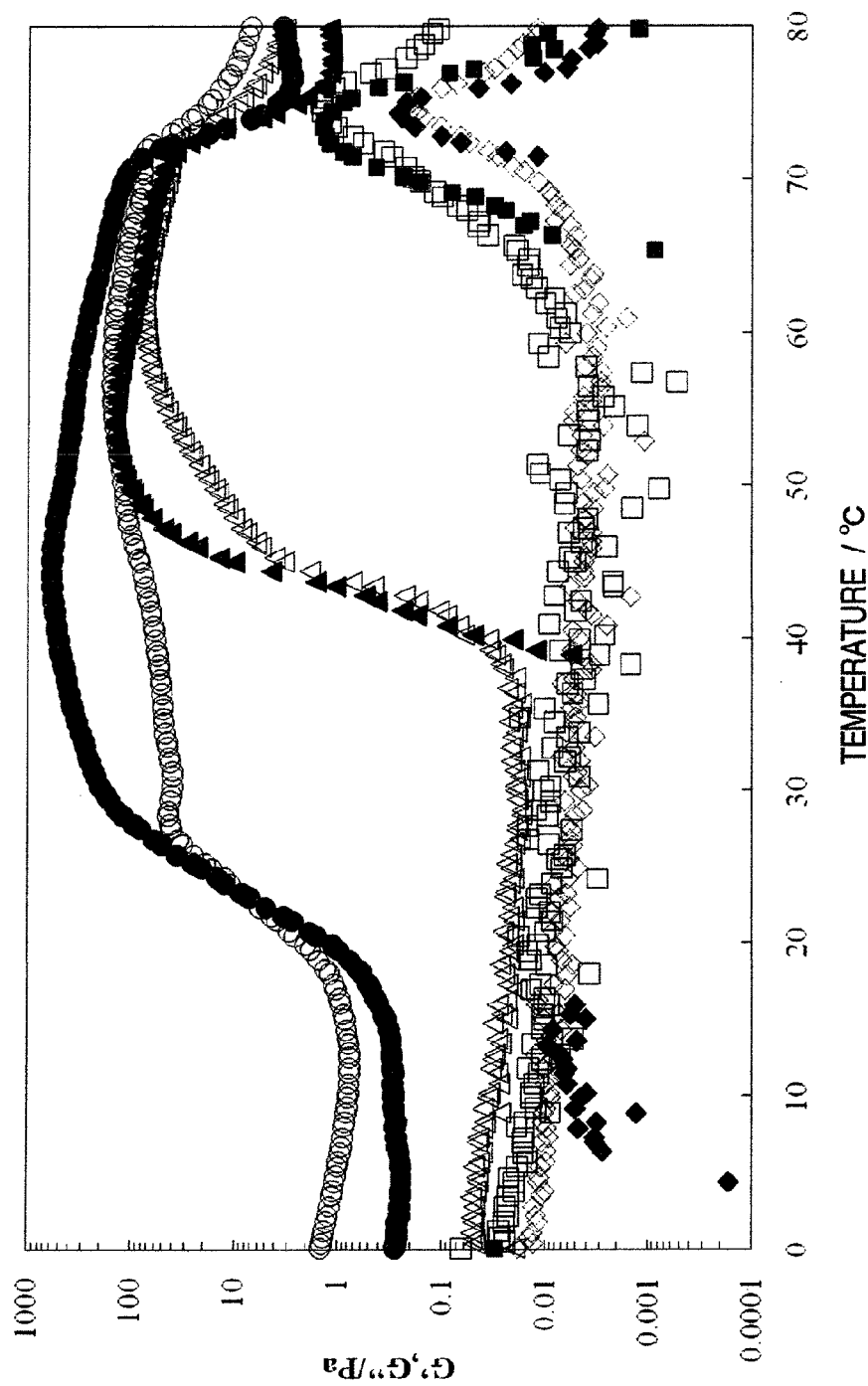

DUAL-TERMINAL AMIDE HYDROGELLING AGENT

TECHNICAL FIELD

The present invention relates to hydrogelating agents having novel chemical structures and composition, and hydrogel based on the same.

BACKGROUND ART

Low-molecular-weight gelator forms gel by the self-assembly due to intramolecular interaction and captures solvent molecules in the three-dimensional network (see, for example, Non Patent Literature 1).

Since a low-molecular-weight gelator can be designed, it is expected to be applied to various fields such as a separation membrane, a sensor, a catalyst, an electronic material and a biomaterial (see, for example, Non Patent Literature 2).

We have already synthesized benzamide derivatives which have long alkyloxy chains at 3-, 4- and 5-positions (see Patent Literature 1) having a novel structure and found that a part of the synthesized compounds could gelate organic solvents. Furthermore, we found that the gelation depended on their chemical structures (see Patent Literature 2).

However, for the biomaterial application, it is apparent that hydrogel in which water is gelated is more desirable than organogel in which an organic solvent is gelated. There are not many reports on low-molecular-weight hydrogel (see, for example, Non Patent Literature 3). Furthermore, if the obtained hydrogel is used as a biomaterial, it is desirable that the hydrogel itself has biocompatibility. There are not many reports from this point of view either.

We have synthesized 3,4,5-long-alkyloxy-chain benzamide derivatives having oligo- or poly(ethylene glycol) moiety. We have disclosed that these compounds can be used for imparting biocompatibility to medical materials, etc. (see Patent Literature 3), and that these compounds gelates organic solvents (see Patent Literature 4). Besides these, we further found that these compounds formed hydrogel (see Patent Literatures 5, 6). However, to optimize the physical properties of hydrogel, preparation processes according to the purpose and use, the development of novel hydrogelating agents has been desired.

With the recent progress in the stem cell study, the application of hydrogel to cell culture has attracted much attention (see, for example, Non Patent Literature 4). In the case of cell culture, hydrogel must be formed at a cell culture temperature. In particular, hydrogel, which is solution state (sol) at a temperature lower than or close to a room temperature and gels at a cell culture temperature, is highly useful, because cultured cells can be collected by lowing the temperature after cell culture (see, for example, Patent Literature 7). Conversely, for storing cells, hydrogel, which is liquid state (sol) around a room temperature to a cell culture temperature and gels at a cell storage temperature, is preferred. Hydrogel behavior can be controlled like these has been desired.

CITATION LIST

Patent Literature

Patent Literature 1: JP 2001-122889 A
Patent Literature 2: JP 2004-262809 A
Patent Literature 3: JP 2005-232061 A
Patent Literature 4: JP 2005-232278 A
Patent Literature 5: JP 2007-217551 A
Patent Literature 6: JP 2009-84272 A
Patent Literature 7: JP 1994-141851 A

Non-Patent Literature

Non Patent Literature 1: Chem. Rev., 1997, Vol. 97, p. 3133-3159
Non Patent Literature 2: Angew. Chem. Int. Ed., 2000, Vol. 39, p. 2263-2266
Non Patent Literature 3: Chem. Rev., 2004, Vol. 104, p. 1201-1217
Non Patent Literature 4: Nature, 2009, Vol. 462, p. 433-441

SUMMARY OF INVENTION

Technical Problem

An object of the present invention is to provide hydrogelating agents having novel chemical structures and composition, and hydrogel based on the same.

Solution to Problem

The present inventors have synthesized benzamide derivatives represented by Formula (0) and having oligo- or poly (ethylene glycol) and long-chain alkyloxy moieties, and found that they formed hydrogel (JP 2009-84272 A).

In the present invention, the inventors newly and separately synthesized compounds represented by Formula (1), which have benzamide moieties at both terminals of oligo- or poly (ethylene glycol) and the formation of hydrogel was checked. As a result, the inventors found that the behavior is completely different from that of the compounds represented by Formula (0). Furthermore, the inventors found that the gelation temperature and the strength of gel can be controlled by mixing the two types of compounds. Based on the findings, the present invention was accomplished.

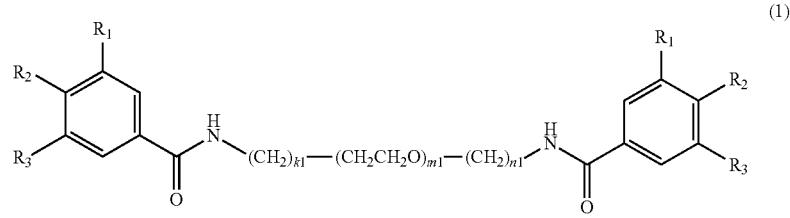

(1)

wherein k1 represents an integer of 0 to 4; m1 represents an integer of 1 to 100; and n1 represents an integer of 1 to 6; $R_1$ represents a hydrocarbon group having 8 to 22 carbon atoms and bonded via an oxygen atom; $R_2$ represents H or a hydrocarbon group having 1 to 22 carbon atoms and bonded via an oxygen atom; $R_3$ represents H or a hydrocarbon group having 1 to 22 carbon atoms and bonded via an oxygen atom; and $R_2$ and $R_3$ are not H at the same time.

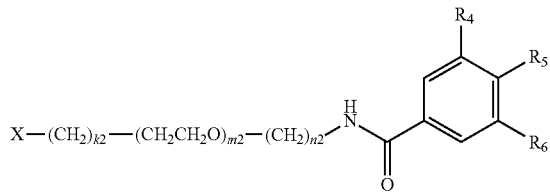

More specifically, the present invention provides a benzamide derivative represented by Formula (1), a hydrogelating agent containing the derivative, and hydrogel containing the hydrogelating agent and water.

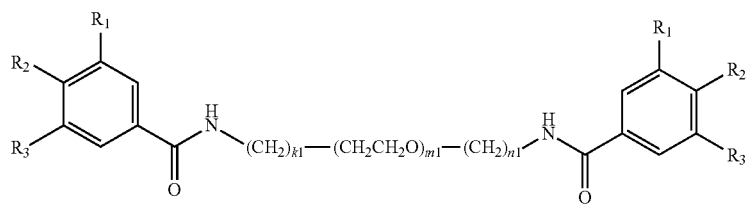

wherein k1 represents an integer of 0 to 4; m1 represents an integer of 1 to 100; and n1 represents an integer from 1 to 6; $R_1$ represents a hydrocarbon group having 8 to 22 carbon atoms and bonded via an oxygen atom; $R_2$ represents H or a hydrocarbon group having 1 to 22 carbon atoms and bonded via an oxygen atom; $R_3$ represents H or a hydrocarbon group having 1 to 22 carbon atoms and bonded via an oxygen atom; and $R_2$ and $R_3$ are not H at the same time.

Furthermore, the present invention provides a hydrogelating agent containing a benzamide derivative represented by Formula (1) and a benzamide derivative represented by Formula (2):

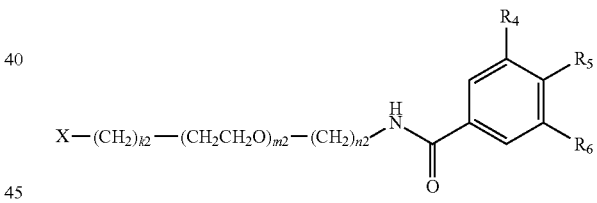

wherein X represents OH or $NH_2$; k2 represents an integer of 0 to 4; m2 represents an integer of 1 to 100; and n2 represents an integer of 1 to 6; $R_4$ represents a hydrocarbon group having 8 to 22 carbon atoms and bonded via an oxygen atom; $R_5$ represents H or a hydrocarbon group having 1 to 22 carbon atoms and bonded via an oxygen atom; $R_6$ represents H or a hydrocarbon group having 1 to 22 carbon atoms and bonded via an oxygen atom; and $R_5$ and $R_6$ are not H at the same time, and provides hydrogel containing the hydrogelating agent and water.

Furthermore, the present invention provides a benzamide derivative represented by Formula (3):

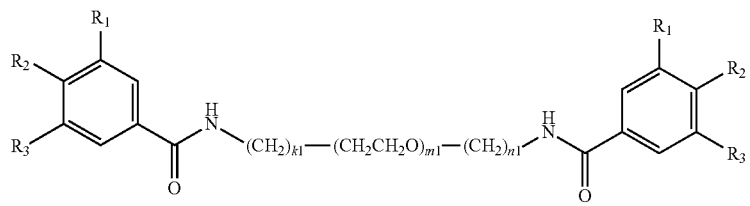

wherein X represents OH or $NH_2$; k2 represents 0; m2 represents an integer of 10 to 100; and n2 represents 2; $R_4$ and $R_6$ represent a hydrocarbon group having 12 to 18 carbon atoms and bonded via an oxygen atom; $R_5$ represents a hydrocarbon group having 1 to 18 carbon atoms and bonded via an oxygen atom; and $R_4$ and $R_5$ represent different hydrocarbon groups.

wherein k1 represents an integer of 0 to 4; m1 represents an integer of 7 to 100; and n1 represents an integer of 2 to 6; $R_1$ and $R_3$ represent a hydrocarbon group having 12 to 18 carbon atoms and bonded via an oxygen atom; and $R_2$ represents H or a hydrocarbon group having 1 to 18 carbon atoms and bonded via an oxygen atom, and provides a hydrogelating agent containing the derivative and hydrogel containing the hydrogelating agent and water.

The present invention also provides a hydrogelating agent containing a benzamide derivative represented by Formula (3) and a benzamide derivative represented by Formula (4):

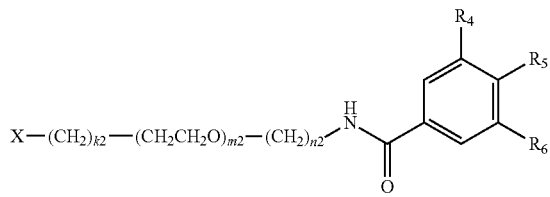

(4)

wherein X represents OH or $NH_2$; k2 represents an integer of 0 to 4; m2 represents an integer of 7 to 100; and n2 represents an integer of 2 to 6; $R_4$ and $R_6$ represent a hydrocarbon group having 12 to 18 carbon atoms and bonded via an oxygen atom; $R_5$ represents H or a hydrocarbon group having 1 to 18 carbon atoms and bonded via an oxygen atom, and further provides hydrogel containing the hydrogelating agent and water.

Furthermore, the present invention provides hydrogel containing a benzamide derivative represented by Formula (1); hydrogel containing a benzamide derivative represented by Formula (1) and a benzamide derivative represented by Formula (2); hydrogel containing a benzamide derivative represented by Formula (3); or hydrogel containing a benzamide derivative represented by Formula (3) and a benzamide derivative represented by Formula (4), wherein a sol-to-gel transition temperature associated with temperature rise is 10° C. or more and 40° C. or less; and a method for culturing cells using the hydrogel.

Particularly, the present invention provides a hydrogelating agent containing a benzamide derivative represented by Formula (5) and a benzamide derivative represented by Formula (6); and hydrogel containing the hydrogelating agent and water and having a sol-to-gel transition temperature of 10° C. or more and 40° C. or less, and preferably 20° C. or more and 35° C. or less associated with temperature rise; and a method for culturing cells using the hydrogel.

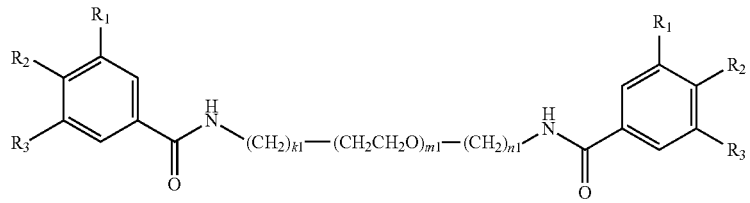

(5)

wherein k1 is 0; m1 is 42 to 45; n1 is 2; $R_1$ is $OC_{14}H_{49}$; $R_2$ is $OCH_3$; and $R_3$ is $OC_{14}H_{49}$.

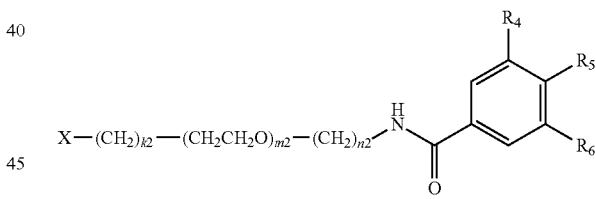

(6)

wherein X is OH; k2 is 0; m2 is 42 to 45; n2 is 2; $R_4$ is $OC_{14}H_{49}$; $R_5$ is $OCH_3$; and $R_6$ is $OC_{14}H_{49}$.

Furthermore, the present invention provides hydrogel containing a benzamide derivative represented by Formula (1); hydrogel containing a benzamide derivative represented by Formula (1) and a benzamide derivative represented by Formula (2); hydrogel containing a benzamide derivative represented by Formula (3); or hydrogel containing a benzamide derivative represented by Formula (3) and a benzamide derivative represented by Formula (4), wherein a sol-to-gel transition temperature associated with temperature drop is −5° C. or more and 35° C. or less; and a method for storing cells using the hydrogel.

Particularly, the present invention provides a hydrogelating agent containing a benzamide derivative represented by Formula (7) and a benzamide derivative represented by Formula (8); and hydrogel containing the hydrogelating agent and water and having a sol-to-gel transition temperature of −5° C. or more and 35° C. or less and preferably 0° C. or more and 20° C. or less associated with temperature drop; and a method of culturing cells using the hydrogel.

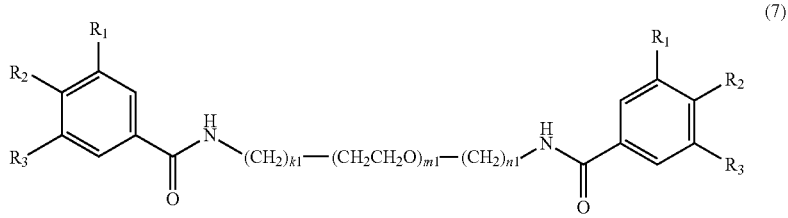

(7)

wherein k1 is 0; m1 is 29 to 32; n1 is 2; $R_1$ is $OC_{14}H_{49}$; $R_2$ is $OCH_3$; and $R_3$ is $OC_{14}H_{49}$.

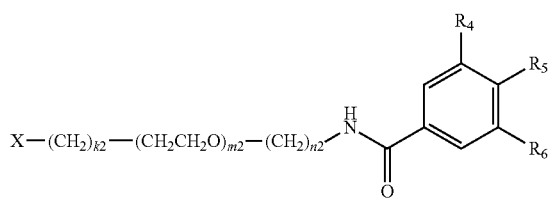

(8)

wherein X is OH; k2 is 0; m2 is 29 to 32; n2 is 2; $R_4$ is $OC_{14}H_{49}$; $R_5$ is $OCH_3$; and $R_6$ is $OC_{14}H_{49}$.

Advantageous Effects of Invention

The present invention adds a new variety of molecules to compounds having oligo- or poly(ethylene glycol) as a partial structure which self-assemble into hydrogel and is suitable for three-dimensional culture of cells, etc.

BRIEF DESCRIPTION OF DRAWINGS

FIG. 7 shows the results of rheological measurements of the hydrogelating agent, which was obtained by the same synthetic method as in Example 7 and contains a compound corresponding to Formula (1) and a compound corresponding to Formula (2) in a ratio of about 0.48:1.

FIG. 8 shows the results of rheological measurements of the hydrogelating agent, which was obtained by the same synthetic method as in Example 11 and contains a compound corresponding to Formula (1) and a compound corresponding to Formula (2) in a ratio of about 0.16:1.

FIG. 9 shows the results of rheological measurements of the hydrogelating agent, which was obtained by the same synthetic method as in Example 11 and contains a compound corresponding to Formula (1) and a compound corresponding to Formula (2) in a ratio of about 0.45:1.

MODE FOR CARRYING OUT THE INVENTION

Figure 1:
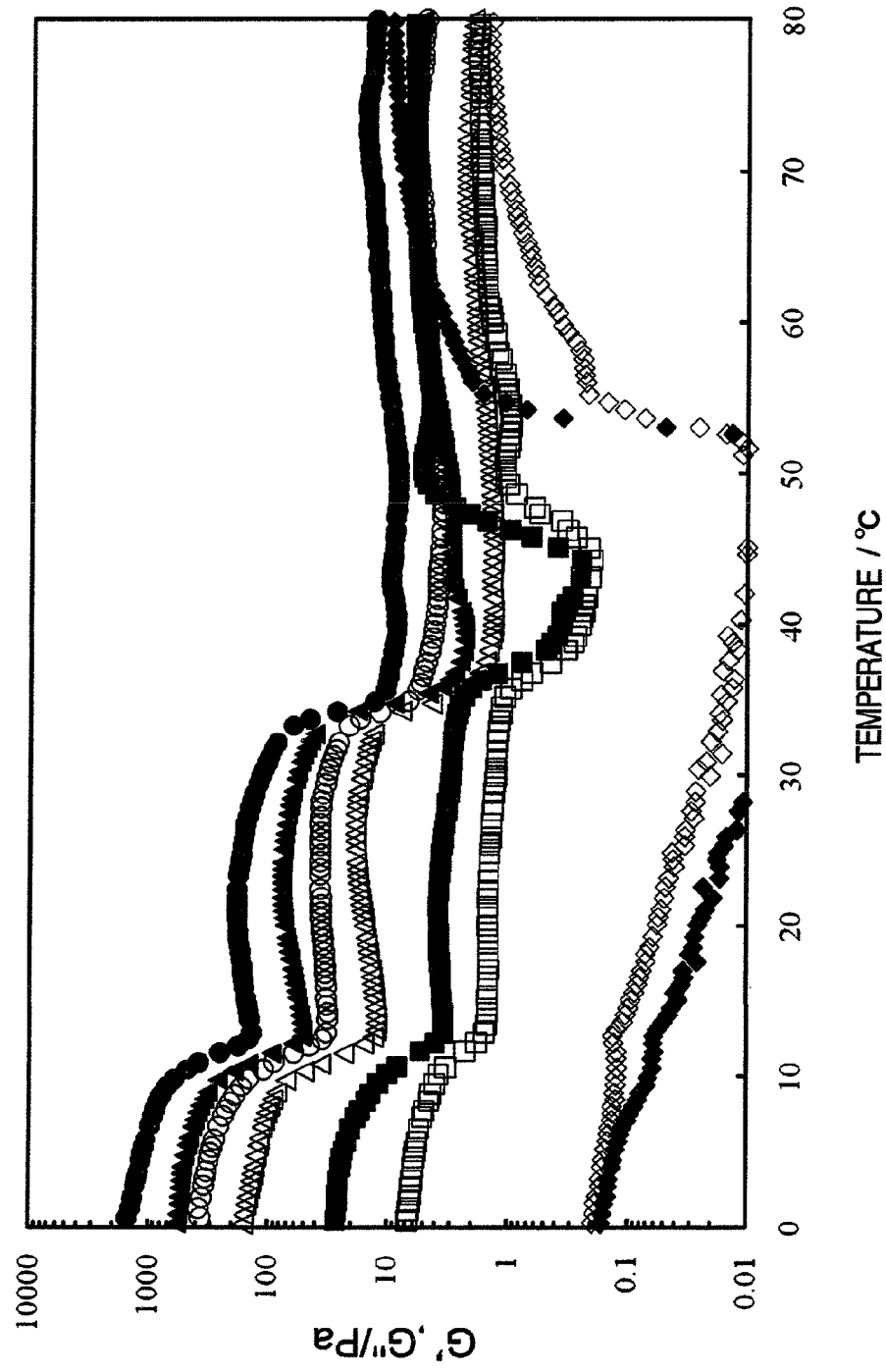
FIG. 1 shows the results of rheological measurements of the hydrogelating agent obtained in Example 1.

The present invention relates to a benzamide derivative represented by the following Formula (9).

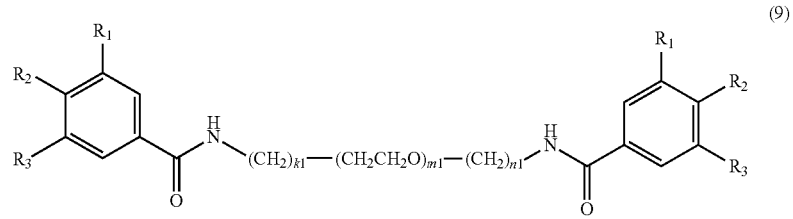

(9)

wherein k1 represents an integer of 0 to 4; m1 represents 1 to 100, preferably 7 to 100; and n1 represents 1 to 6, preferably 2 to 6; $R_1$ represents a hydrocarbon group having 8 to 22 carbon atoms, preferably 12 to 18 carbon atoms and bonded via an oxygen atom; $R_2$ represents H or a hydrocarbon group having 1 to 22 carbon atoms, preferably 1 to 18 carbon atoms and bonded via an oxygen atom; $R_3$ represents H or a hydrocarbon group having 1 to 22 carbon atoms, preferably 1 to 18 carbon atoms and bonded via an oxygen atom; and $R_2$ and $R_3$ are not H at the same time. Furthermore, preferably $R_1$ and $R_3$ represents a hydrocarbon group having 12 to 18 carbon atoms and bonded via an oxygen atom; and $R_2$ represents H or a hydrocarbon group having 1 to 18 carbon atoms and bonded via an oxygen atom.

Hereinafter, a compound having a benzamide group at both terminals and represented by Formula (1), Formula (3), Formula (5), Formula (7) or Formula (9) will also be referred to as a "dual-terminal amide compound" or a "dual-terminal amide derivative" and a compound having a benzamide group only at one of the terminals and represented by Formula (2), Formula (4), Formula (6) or Formula (8) will also be referred to as a "uni-terminal amide compound" or a "uni-terminal amide derivative".

Note that, in view of hydrogel formation around room temperature, m1 is preferably 7 or more; the number of carbon atoms of $R_1$ is preferably 12 to 18; and the number of carbon atoms of each of $R_2$ and $R_3$ is preferably 18 or less. In view of the synthesis process, n1 is preferably 2 or more.

A benzamide derivative represented by Formula (1) can be obtained, for example, by the amide condensation of a benzoic acid derivative having hydrocarbon groups via an oxygen atom with a derivative of oligo- and poly(ethylene glycol) having amino groups at both terminals. In the condensation, a condensing agent such as a carbodiimide derivative can be used. In addition, an acid anhydride, an acid chloride and an activated ester of the benzoic acid derivative can also be used.

At this time, k1 and n1 can be adjusted according to a synthetic method of a derivative of oligo- or poly(ethylene glycol) having amino groups at both terminals. Furthermore, depending upon starting materials or reaction conditions, a compound having a benzamide group at both terminals and a compound having a benzamide group only at one terminal may be produced as a composition. Even in this case, if necessary, a known fractionation method such as high performance liquid chromatography can be used to separate one of them from the composition or to obtain a composition in which the proportion of one of them has been increased.

A derivative of oligo- or poly(ethylene glycol) having amino groups at both terminals is obtained by sequentially tosylating or mesylating both terminals of a commercially available oligo- or poly(ethylene glycol), iodinating the tosyl or the mesyl group, converting the iodine group into a phthalimide and deprotecting with hydrazine. Alternatively, following tosylation or mesylation, the tosyl or the mesyl group is azidated and then reduced to obtain a similar compound. Particularly, mesylation of an ethylene glycol oligomer or polymer makes it easier to obtain a compound having amino groups at both terminals (J. Am. Chem. Soc., 2009, Vol. 131, p. 2110-2112).

Furthermore, in the case of oligo- or poly(ethylene glycol) having a length not commercially available, the compound is obtained by protecting one of the terminals of commercially available oligo- or poly(ethylene glycol), tosylating the other terminal, condensing with other oligo- or poly(ethylene glycol), which will provide a required length in total, and after deprotection and the condensation (J. Org. Chem., 2004, Vol. 69, p. 639-647). The resultant compound is sequentially tosylating or mesylating both terminals, iodinating the tosyl or the mesyl group, converting the iodine group into phthalimide and deprotecting with hydrazine (Biochemistry, 1980, Vol. 19, p. 4595-4600) to obtain a compound having amino groups at both terminals.

A benzoic acid derivative having the same hydrocarbon groups bonded to the 3-, 4- and 5-position via an oxygen atom is obtained by etherifying a 3,4,5-trihydroxybenzoic acid ester and hydrolyzing the ester.

A benzoic acid derivative having hydrogen at the 5-position and having the same hydrocarbon group bonded to the 3- and the 4-position via an oxygen atom is obtained by simultaneously etherifying the 3- and 4-positions of 3,4-dihydroxybenzoic acid ester, used as a starting material and hydrolyzing the ester. Furthermore, a benzoic acid derivative having a different hydrocarbon group bonded to the 3-position and the 4-position via an oxygen atom is obtained, for example, by taking an advantage of difference in reactivity between the 3-position and the 4-position, more specifically, by selectively etherifying the 4-position, subsequently, etherifying the 3-position with a different hydrocarbon group from that used for the 4-position, followed by hydrolyzing the ester.

A benzoic acid derivative having the 5-position hydrocarbon group, which is different from those bonded to the 3- and the 4-position, via an oxygen atom is obtained, for example, by protecting the 3- and the 4-position of 3,4,5-trihydroxybenzoic acid ester, by the selective crosslinking of a boronic acid derivative to the 3- and 4-positions, etherifying the 5-position, deprotecting the boronic acid derivative, etherifying the 3- and the 4-position in the same manner as above, followed by the hydrolysis of the ester.

A benzoic acid derivative having hydrogen at the 4-position and the hydrocarbon group bonded to the 3- and the 5-position via an oxygen atom is obtained by simultaneously etherifying the 3- and the 5-position of 3,5-dihydroxybenzoic acid ester, used as a starting material, followed by hydrolyzing the ester. Furthermore, a benzoic acid derivative having a different hydrocarbon group bonded to the 3-position and the 5-position via an oxygen atom is obtained, for example, by performing etherification by supplying a hydrocarbon reagent, which is less than the equivalent, isolating a benzoic acid derivative having one of the hydroxyl groups etherified, etherifying the remaining hydroxyl group with a different hydrocarbon reagent, followed by the hydrolysis of the ester.

A benzoic acid derivative having the 4-positon hydrocarbon group, which is different from those of the 3- and the 5-position, via an oxygen atom is obtained, for example, by taking advantage of difference in reactivity of the 4-position of 3,4,5-trihydroxybenzoic acid ester, more specifically, first by etherifying the 4-position, and then etherifying the 3- and the 5-position in the same manner as above, followed by the hydrolysis of the ester.

A dual-terminal amide compound represented by Formula (1) can be singly used as a hydrogelating agent. Alternatively this can be used in the form of a composition with a uni-terminal amide compound represented, for example, by Formula (2) as a hydrogelating agent (hereinafter also referred to as a "mixed hydrogelating agent"). Note that in the case of a composition, a benzamide derivative represented by Formula (2) can be synthesized in the same synthetic route as a benzamide derivative represented by Formula (1); however, both benzamide derivatives may be separately synthesized and mixed. Alternatively, if they are obtained in the form of a composition during the synthesis process of the former or latter, the composition may be used.

A mixed hydrogelating agent can be prepared by mixing a dual-terminal amide compound represented by Formula (1) and a uni-terminal amide compound represented by Formula (2) in an arbitrary mixing ratio. However, to obtain a remarkable effect of mixing a dual-terminal amide compound, the mixed hydrogelating agent preferably contains a dual-terminal amide derivative and a uni-terminal amide derivative in a mixing ratio of larger than 1:8.

Hydrogel can be produced by suspending an appropriate amount of hydrogelating agent containing a benzamide derivative represented by Formula (1) as an active ingredient or a hydrogelating agent containing a mixture of a benzamide derivative represented by Formula (1) and a benzamide derivative represented by Formula (2) as an active ingredient, in water, and directly heating the suspension to a temperature at which the hydrogel is used, or once heating the suspension to a temperature at which the hydrogelating agent is dissolved and then cooling to room temperature, or by further heating to a higher temperature, or by further cooling to a lower temperature. Methods for preparing hydrogel are not limited to these.

The proportion of a hydrogelating agent in hydrogel is preferably within the range of 0.5 to 25 wt % in view of the hydrogel formation and the cost. Furthermore, the proportion of water in hydrogel is preferably within the range of 75 to 99.5 wt %. Furthermore, components such as an antiseptic agent other than a hydrogelating agent and water may be added as long as a significant effect is not exerted on the hydrogel formation.

By controlling the mixing ratio of a dual-terminal amide compound represented by Formula (1) and a uni-terminal amide compound represented by Formula (2), the transition temperature of gelation can be controlled. For example, the gel transition temperature of 52° C. of the mixed hydrogelating agent containing a dual-terminal amide compound represented by Formula (1), wherein k1=0, m1=42 to 45, n1=2, $R_1=R_3=OC_{14}H_{29}$ and $R_2=OCH_3$, and a uni-terminal amide compound represented by Formula (2), wherein $X=NH_2$, k2=0, m2=42 to 45, n2=2, $R_4=R_6=OC_{14}H_{29}$ and $R_5=OCH_3$, in a ratio of about 1:3 (uni-terminal amide:dual-terminal amide=67:33) can be lowered to 40° C. by adding the dual-terminal amide compound to become the about 1:8 composition (uni-terminal amide:dual-terminal amide=89:11) at a concentration of 10 wt % (Example 6).

Furthermore, the transition temperature of gelation associated with temperature drop can be lowered by reducing the concentration of a hydrogelating agent. For example, in a mixed hydrogelating agent containing the dual-terminal amide compound 2 represented by Formula (1) wherein k1=0, m1=29 to 32, n1=2, $R_1=R_3=OC_{14}H_{29}$ and $R_2=OCH_3$ and uni-terminal amide compound 2 represented by Formula (2) wherein X=OH, k2=0, m2=29 to 32, n2=2, $R_4=R_6=OC_{14}H_{29}$ and $R_5=OCH_3$ in a ratio of 0.48:1, a gel transition temperature (gel at a low temperature side, sol at a high temperature side) can be lowered from 52° C. at a concentration of 8 wt % to 32° C. at the concentration of 2 wt % (Example 8).

Furthermore, the transition temperature of gelation associated with temperature rise can be lowered by increasing the concentration of a hydrogelating agent. For example, in the hydrogelating agent containing the dual-terminal amide compound represented by Formula (1) wherein k1=0, m1=42 to 45, n1=2, $R_1=R_3=OC_{14}H_{29}$ and $R_2=OCH_3$ and the uni-terminal amide compound represented by Formula (2) wherein X=OH, k2=0, m2=42 to 45, n2=2, $R_4=R_6=OC_{14}H_{29}$ and $R_5=OCH_3$ in a ratio of 0.45:1, a gel transition temperature (sol at a low temperature side, gel at a high temperature side) can be lowered from 41° C. at a concentration of 8 wt % to 23° C. at the concentration to 15 wt % (Example 12).

Likewise, hydrogel having a desired gel transition temperature can be obtained by appropriately changing the composition ratio of a dual-terminal amide compound and a uni-terminal amide compound and the concentration of a hydrogelating agent.

The hydrogel provided by the present invention can be used for culturing and storing cells. The "cells" used herein are referred to "discrete single cells", "cell aggregate", "a part of tissue composed of cells", "tissue composed of cells", and the like.

Cells can be cultured on hydrogel, which forms hydrogel at a temperature at which cells are cultured. Alternatively, cells can be cultured within hydrogel if the hydrogel is present in a sol state at a low temperature. More specifically, cells are seeded in the sol-state and the hydrogel is formed at a cell culture temperature. In this manner, the cells are cultured in the hydrogel. In the case where cells are cultured on hydrogel, cultured cells can be separated and collected by removing them from the surface. In contrast, in the case where cells are cultured within hydrogel, cultured cells can be separated and collected by lowering a temperature to return the hydrogel in a sol state.

For example, the composition ratio of a dual-terminal amide compound represented by Formula (5) and a uni-terminal amide compound represented by Formula (6) contained in a mixed hydrogelating agent, and the composition ratio of the hydrogelating agent and water contained in hydrogel can be selected such that the sol-to-gel transition temperature associated with temperature rise becomes close to room temperature (25° C.). The aforementioned cell culture method can be realized by using the hydrogel.

More specifically, for example, a hydrogelating agent containing a dual-terminal amide compound represented by Formula (1) wherein k1=0, m1=42 to 45, n1=2, $R_1=R_3=OC_{14}H_{29}$ and $R_2=OCH_3$, and a uni-terminal amide compound represented by Formula (2) wherein X=OH, k2=0, m2=42 to 45, n2=2, $R_4=R_6=OC_{14}H_{29}$ and $R_5=OCH_3$ in a ratio of 0.45:1, has a gel transition temperature of near 23° C. at a concentration of 15 wt %. The hydrogelating agent is present in a gel state at a high temperature side (37° C.) suitable for culturing animal cells and in a sol state at a low temperature side suitable for collecting cells (Example 12).

For storing cells, a hydrogelating agent transferring from sol to gel by lowering temperature is used. For example, cells can be stored by pouring a sol-state hydrogelating agent solution onto cells and lowering a temperature to form hydrogel or by mixing cells in soft hydrogel, or by seeding cells in sol-state gel from room temperature to a cell culture temperature and then lowering a temperature to form hydrogel. The cells stored under hydrogel can be collected by physically removing the hydrogel or diluting the hydrogel with cell culture medium. The cells stored within hydrogel can be collected by diluting the hydrogel with cell culture medium or by raising a temperature to convert the hydrogel into a sol state.

For example, the composition ratio of a dual-terminal amide compound represented by Formula (7) and a uni-terminal amide compound represented by Formula (8) contained in a mixed hydrogelating agent, and the composition ratio of the hydrogelating agent and water contained in hydrogel can be selected such that the sol-to-gel transition temperature associated with temperature drop becomes close to room temperature (25° C.). The aforementioned cell storing method can be realized by using the hydrogel.

More specifically, for example, a hydrogelating agent containing a dual-terminal amide compound represented by Formula (1) wherein k1=0, m1=29 to 32, n1=2, $R_1=R_3=OC_{14}H_{29}$ and $R_2=OCH_3$, and a uni-terminal amide compound represented by Formula (2) wherein X=OH, k2=0, m2=29 to 32, n2=2, $R_4=R_6=OC_{14}H_{29}$ and $R_5=OCH_3$ in a ratio of 0.48:1, is in a sol state at 37° C. at a concentration of 2 wt % and in a gel state at 30° C. or less. Thus, a cell storing method for storing cells in gel at a low temperature of 30° C. or less and collecting cells at a cell culture temperature of 37° C. can be realized (Example 8).

The present invention will be further specifically described below, but the present invention is not limited to the following description.

Note that hereinafter, EDC.HCl is an abbreviation for water soluble carbodiimide hydrochloride, HOBt for 1-hydroxybenzotriazole hydrate and PEG for polyethylene glycol.

EXAMPLES

Example 1

Synthesis of a Dual-Terminal Amide Compound Represented by Formula (1) Wherein k1=0, m1=29 to 32, n1=2, $R_1=R_3=OC_{14}H_{29}$ and $R_2=OCH_3$ PEG having a molecular weight of 1540 was used as a starting material. Two hydroxyl groups at both terminals of PEG were mesylated according to the method described in a literature (J. Am. Chem. Soc., 2009, Vol. 131, p. 2110-2112) and then azidated. The azide was reduced to give PEG-diamine having a molecular weight of 1540 (80.0 g, 52.0 mmol). PEG-diamine was dissolved in methylene chloride (350 ml) and then triethylamine was added to adjust pH to 6. To the solution, a methylene chloride solution (350 ml) of acid chloride (65.0 g, 109 mmol), which was obtained by the reaction between 3,5-bis(tetradecyloxy)-4-methoxybenzoic acid (Bioorg. Med. Chem., 2002, Vol. 10, p. 4013-4022) and thionyl chloride according to the method described in a literature (Org. Lett., 2004, Vol. 6, p. 4171-4174), was added dropwise over 20 minutes. Triethylamine was further added and further stirred at room temperature for 2 hours while keeping pH at near 9. The reaction solution was washed with 1 N hydrochloric acid, aqueous saturated sodium bicarbonate and brine, and dried over sodium sulfate. The solvent was removed in vacuo and the residue was further treated with activated charcoal to give a desired compound (116.7 g, yield 84%).

$^1$H-NMR (CDCl$_3$) δ=7.02 (4H, s, 2.6-H), 6.92 (2H, br-t, NH), 4.02 (8H, t, J=6.6 Hz, 3.5-OCH$_2$), 3.84 (6H, s, 4-OCH$_3$), 3.70~3.55 (~128H, m, CH$_2$OCH$_2$), 1.80 (8H, quintet, J=7.6 Hz, 3.5-OCCH$_2$), 1.44 (8H, quintet, J=7.2 Hz, 3.5-OC$_2$CH$_2$), 1.36~1.22 (80H, m, 3.5-OC$_3$C$_{10}$H$_{20}$), 0.86 (12H, t, J=6.8 Hz, 3.5-OC$_{13}$CH$_3$).

Example 2

Rheological Measurement of the Dual-Terminal Amide Compound Obtained in Example 1

To analyze the sol-gel transition behavior of the dual-terminal amide compound obtained in Example 1, the viscoelasticity of aqueous sample solutions was measured. The sample concentrations were adjusted to 5 wt %, 10 wt %, 15 wt % and 20 wt %. After sufficiently stirred, the aqueous sample solutions were stored in a freezer. The rheological measurement was performed by use of ARES-G2 (TA Instruments, Japan). Parallel plates (50 mm) were used and a frequency was set to be 1 Hz. Measurement was performed while raising the temperature of the aqueous sample solutions from 0 to 80° C. at a temperature raising rate of 3° C./min.

The results are shown in FIG. 1. In the figure, G' indicates a storage modulus, G" indicates a loss modulus. G'>G" indicates a gel state; G'<G" indicates a sol state and G'=G" indicates a gel transition point.

As a result, it was found that the hydrogelating agent obtained in Example 1 formed hydrogel at a wide concentration range, at least 5 wt % or more. The hydrogelating agent formed gel at 48° C. or more at a concentration of 5 wt %, and the hydrogelating agent provides hydrogel at a wider temperature range at other concentrations.

Example 3

Synthesis of a Dual-Terminal Amide Compound Represented by Formula (1) Wherein k1=0, m1=42 to 45, n1=2, R$_1$=R$_3$=OC$_{14}$H$_{29}$ and R$_2$=OCH$_3$ PEG having a molecular weight of 2000 was used as a starting material. Two hydroxyl groups at both terminals of PEG were mesylated according to the method described in a literature (J. Am. Chem. Soc., 2009, Vol. 131, p. 2110-2112) and then azidated. The azide was reduced to obtain PEG-diamine having molecular weight of 2000 (80.0 g, 40.0 mmol). PEG-diamine was dissolved in methylene chloride (350 ml), and triethylamine was added to adjust pH to 6. To the solution, a methylene chloride solution (350 ml) of acid chloride (50.0 g, 84.1 mmol), which was obtained by the reaction between 3,5-bis(tetradecyloxy)-4-methoxybenzoic acid and thionyl chloride according to the method described in a literature (Org. Lett., 2004, Vol. 6, p. 4171-4174), was added dropwise over 20 minutes. Further, triethylamine was added and the mixture was stirred at room temperature for 2 hours while keeping pH around 9. The reaction solution was washed with 1 N hydrochloric acid, aqueous saturated sodium bicarbonate and brine and dried over sodium sulfate. The solvent was removed in vacuo and the residue was further treated with activated charcoal to give a desired compound (101.2 g, yield 81%).

$^1$H-NMR (CDCl$_3$) δ=7.01 (4H, s, 2.6-H), 6.80 (2H, br-t, NH), 4.02 (8H, t, J=6.6 Hz, 3.5-OCH$_2$), 3.84 (6H, s, 4-OCH$_3$), 3.70~3.50 (~180H, m, CH$_2$OCH$_2$), 1.79 (8H, quintet, J=7.2 Hz, 3.5-OCCH$_2$), 1.44 (8H, quintet, J=7.6 Hz, 3.5-OC$_2$H$_2$), 1.38~1.20 (80H, m, 3.5-OC$_3$C$_{10}$H$_{20}$), 0.87 (12H, t, J=6.8 Hz, 3.5-OC$_{13}$CH$_3$).

Example 4

Rheological Measurement of the Compound Obtained in Example 3

Figure 2:
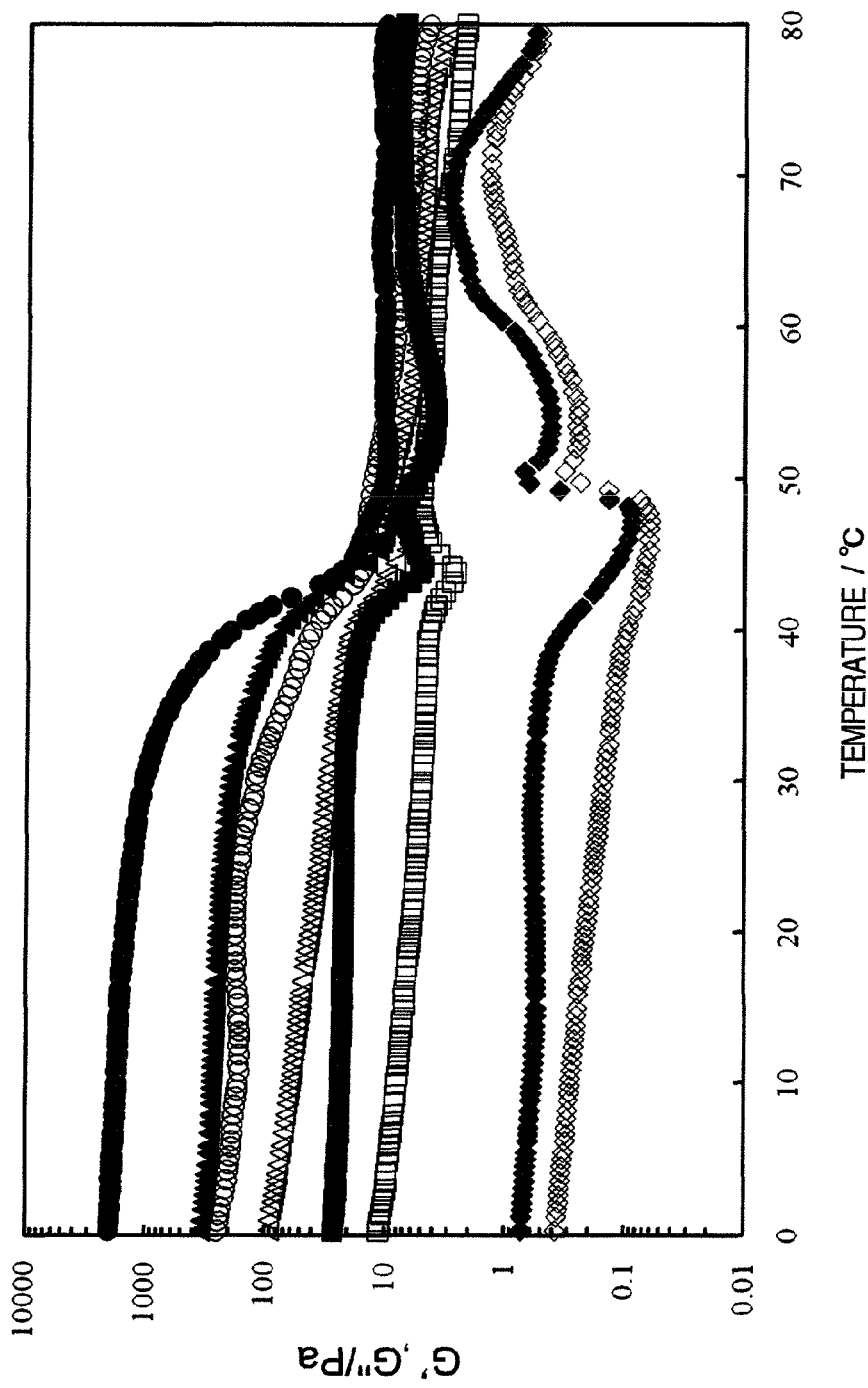
FIG. 2 shows the results of rheological measurements of the hydrogelating agent obtained in Example 3.

To analyze the sol-gel transition behavior of the compound obtained in Example 3, the viscoelasticity of aqueous sample solutions was measured. The sample concentrations were adjusted to 5 wt %, 10 wt %, 15 wt % and 20 wt %. The rheological measurement was performed in the same manner as in Example 2. The results are shown in FIG. 2.

As a result, it was found that the compound (hydrogelating agent) obtained in Example 3 formed hydrogel at a wide concentration range, at least 5 wt % or more, and at a wide temperature range.

Example 5

Synthesis of a Composition Composed of a Compound Represented by Formula (2) Wherein X=NH$_2$, k2=0, m2=42 to 45, n2=2, R$_4$=R$_6$=OC$_{14}$H$_{29}$ and R$_5$=OCH$_3$ and a Compound Represented by Formula (1) wherein k1=0, m1=42 to 45, n1=2, R$_1$=R$_3$=OC$_{14}$H$_{29}$ and R$_2$=OCH$_3$ To a methylene chloride solution (525 ml) of acid chloride (52.4 g, 88.1 mmol), which was obtained by the reaction between 3,5-bis(tetradecyloxy)-4-methoxybenzoic acid and thionyl chloride according to the method described in a literature (Org. Lett., 2004, Vol. 6, p. 4171-4174), N-hydroxysuccinimide (10.2 g, 88.6 mmol) was added at room temperature and stirred for 2 hours. After the solvent was removed in vacuo, activated ester (75.2 g) was obtained.

The activated ester (59.3 g) unpurified was directly dissolved in pyridine (350ml) and mixed with a pyridine solution (400 ml) of PEG-diamine (88.0 g, 44.0 mmol), which was obtained by mesylating the two hydroxyl groups at both terminals of PEG having a molecular weight of 2000 used as a starting material, azidating and reducing according to the method described in a literature (J. Am. Chem. Soc., 2009, Vol. 131, p. 2110-2112). Furthermore, dimethylaminopyridine (528 mg, 4.32 mmol) was added and stirred at 4° C. for 2 hours and further stirred at room temperature for 2 hours.

The reaction mixture was poured into 1 N hydrochloric acid (1000 ml) under ice cooling and extracted with chloroform. The organic layer was washed with 1 N hydrochloric acid and brine and dried over sodium sulfate. The solvent was removed in vacuo and the residue was dissolved in methanol and washed with hexane. Methanol was evaporated to give a desired composition (43.9 g).

$^1$H-NMR (CDCl$_3$) δ=7.02 (2H, s, 2.6-H), 6.92 (1H, br-t, NH), 4.02 (4H, t, J=6.6 Hz, 3.5-OCH$_2$), 3.84 (3H, s, 4-OCH$_3$), 3.70~3.50 (~180H, m, CH$_2$OCH$_2$), 1.80 (4H, quintet, J=7.2 Hz, 3.5-OCCH$_2$), 1.44 (4H, quintet, J=7.6 Hz, 3.5-OC$_2$CH$_2$), 1.38-1.20 (40H, m, 3.5-OC$_3$C$_{10}$H$_{20}$), 0.86 (6H, t, J=6.8 Hz, 3.5-OC$_{13}$CH$_3$).

As a result of HPLC analysis (column: DMSO PAK SP-200-5-C4-P, column temperature: 40° C., solvent: an aqueous 70-99% acetonitrile solution, 0.1% TFA, linear concentration gradient, flow rate: 1.0 ml/min), it was found that the product was a composition containing a uni-terminal amide compound represented by Formula (2) wherein X=NH$_2$, k2=0, m2=42 to 45, n2=2, R$_4$=R$_6$=OC$_{14}$H$_{29}$ and R$_5$=OCH$_3$ and a dual-terminal amide compound represented by Formula (1) wherein k1=0, m1=42 to 45, n1=2, $R_1=R_3=OC_{14}H_{29}$ and $R_2=OCH_3$ in a molar ratio of about 8:1.

Example 6

Rheological Measurement of the Composition Obtained in Example 5 and a Mixture of the Composition and the Dual-Terminal Amide Compound Obtained in Example 3

Figure 3:
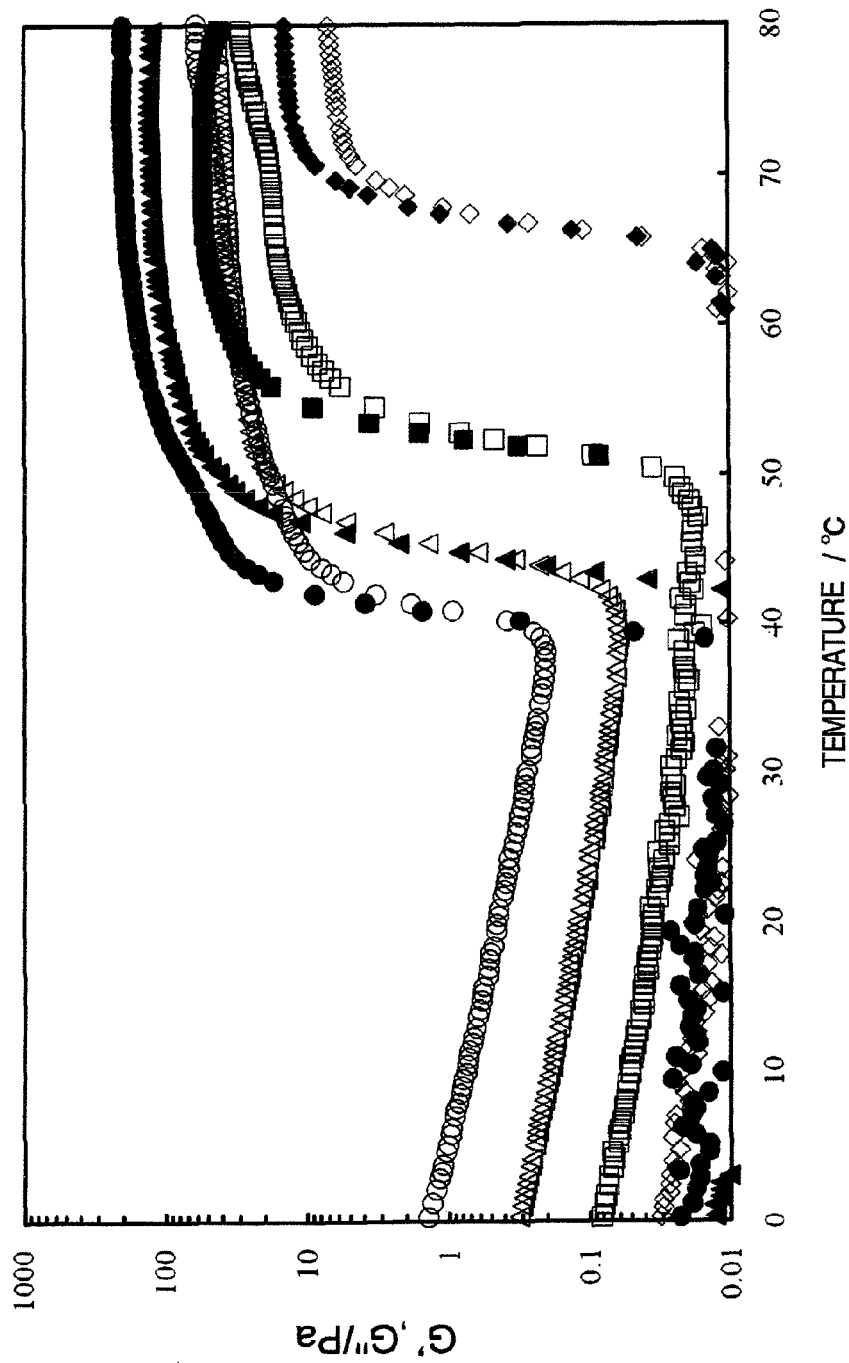
FIG. 3 shows the results of rheological measurements of the hydrogelating agent obtained in Example 5.

To analyze the sol-gel transition behavior of the composition obtained in Example 5, the viscoelasticity of aqueous sample solutions was measured. The sample concentrations were adjusted to 5 wt %, 10 wt %, 15 wt % and 20 wt %. The rheological measurement was performed in the same manner as in Example 2. The results are shown in FIG. 3.

As a result, it was found that the composition (hydrogelating agent) obtained in Example 5 forms hydrogel at a wide concentration range of at least 5 wt % or more. In all of the cases, hydrogel changed from sol to gel by raising temperature. The gel transition point varied depending on the concentration and decreased from 66° C., to 52° C., to 44° C. and to 41° C.

Figure 4:
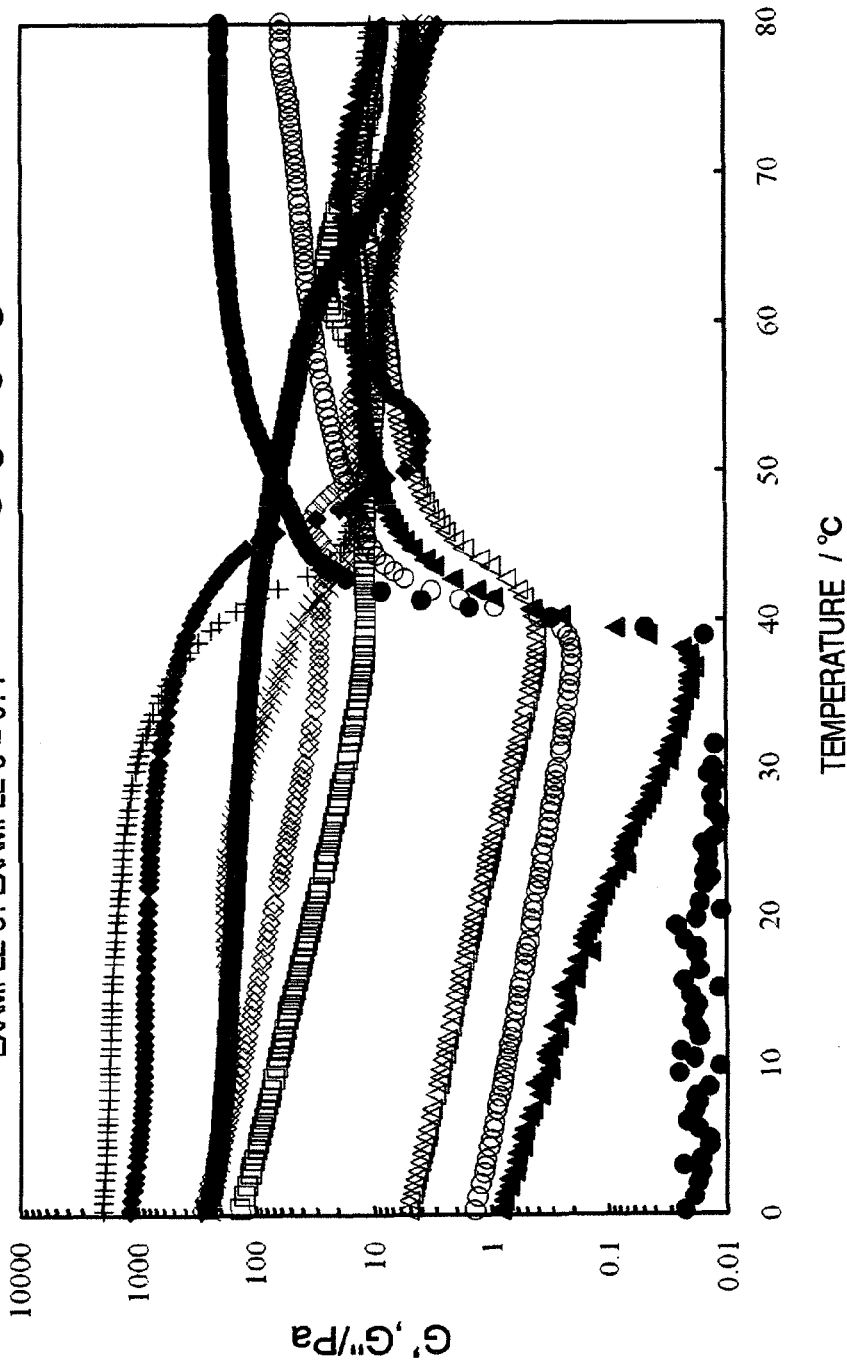
FIG. 4 shows the results of rheological measurements of the mixture of hydrogelating agents obtained in Example 3 and Example 5 (hydrogelating-agent concentration: 20 wt %).
Figure 5:
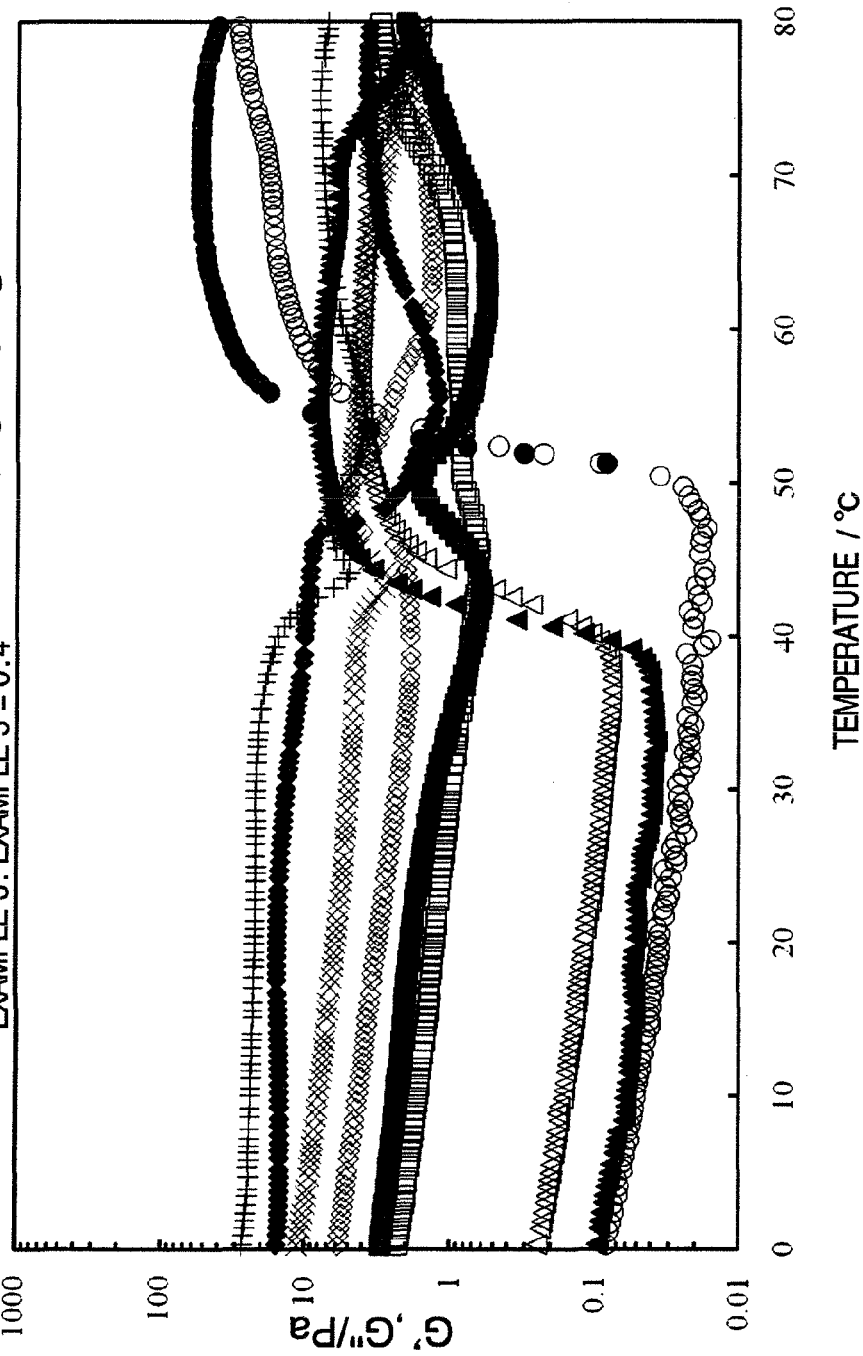
FIG. 5 shows the results of rheological measurements of the mixture of hydrogelating agents obtained in Example 3 and Example 5 (hydrogelating-agent concentration: 10 wt %).
Figure 6:
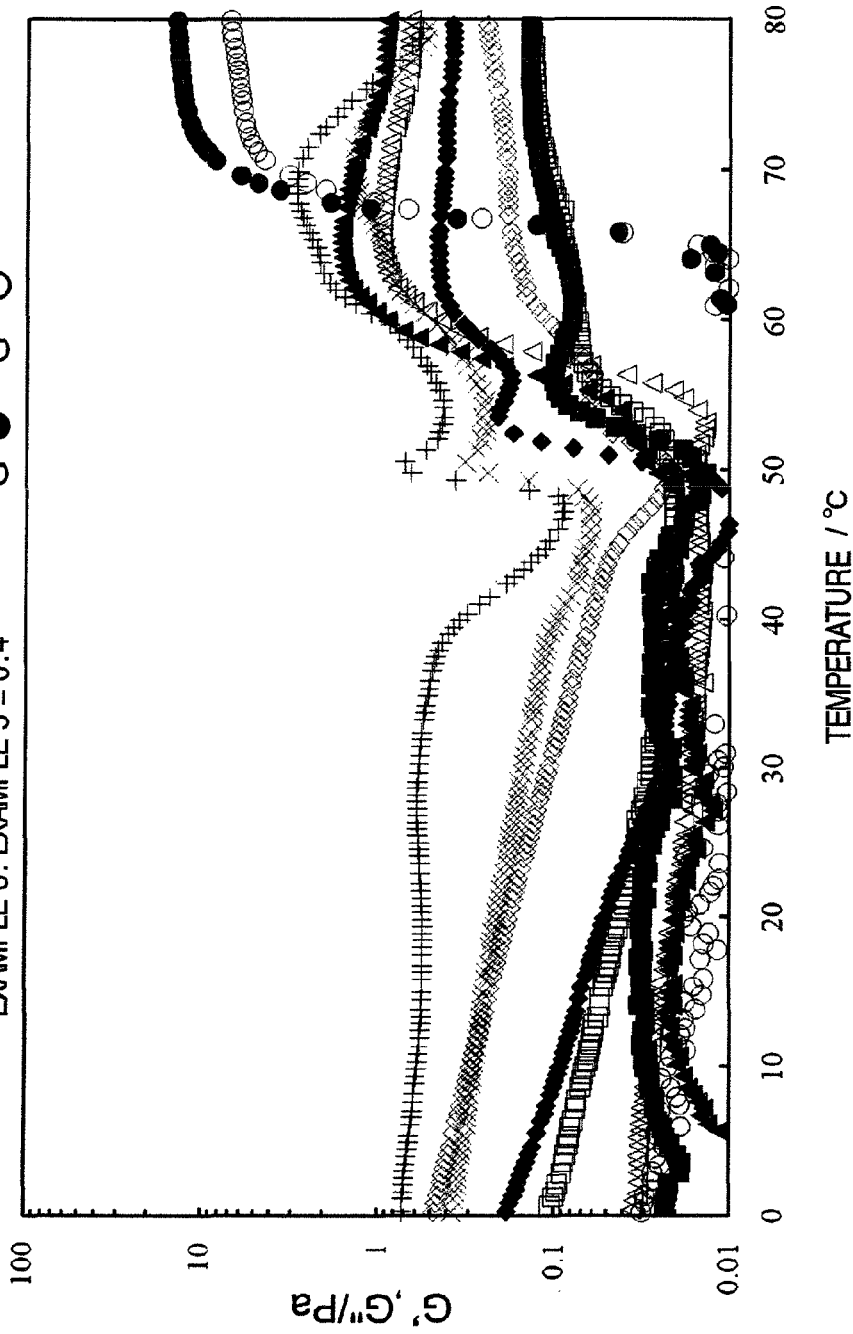
FIG. 6 shows the results of rheological measurements of the mixture of hydrogelating agents obtained in Example 3 and Example 5 (hydrogelating-agent concentration: 5 wt %).

Similarly, viscoelasticity of the compound obtained in Example 3, the composition obtained in Example 5, and the mixture of them was measured. Samples containing the compound and the composition in the ratios of 0:4, 1:3, 2:2, 3:1 and 4:0 were prepared and the total concentrations of them in the samples were set to be 5 wt %, 10 wt % and 20 wt %. The results are shown in FIG. 4 to FIG. 6.

It was found that a mixed hydrogelating agent showed a temperature dependency different from that of the individual hydrogelating agents. Following discussion will be made particularly on the gel transition temperature of hydrogelating agent obtained in Example 5. For example, the sol-to-gel transition temperature of the hydrogelating agent obtained in Example 5 is 52° C. at the concentration of 10 wt % is lowered to 40° C. by mixing 25% of the hydrogelating agent obtained in Example 3. It was found that the gel formation temperature can be controlled by mixing hydrogelating agents. Furthermore, the strength of gel, which correlates with G', can also be controlled by changing a mixing ratio.

Example 7

(Synthesis of a composition of a uni-terminal amide compound represented by Formula (2) wherein X =OH, k2=0, m2=29 to 32, n2=2, $R_4$ = $R_6$ =$OC_{14}H_{29}$ and $R_5$ =$OCH_3$ and a dual-terminal amide compound represented by Formula (1) wherein k1=0, m1=29 to 32, n1=2, $R_1$ =$R_3$ =$OC_{14}H_{29}$ and $R_2$ =$OCH_3$)

PEG (3.08 g, 2.00 mmol) having a molecular weight of 1540 was dissolved in pyridine (10 ml) and p-toluenesulfonyl chloride (0.76 g, 4.00 mmol) was added and stirred at room temperature for 2 hours. After completion of the reaction, chloroform (100 ml) was added and neutralization was performed with 1 M HCl (100 ml). The solution was washed with aqueous 4% $NaHCO_3$ and brine. The organic phase was dried over anhydrous sodium sulfate. After filtration, the solvent was removed in vacuo. The residue was purified by silica gel column chromatography (chloroform:methanol =10:1) to give mono-tosylated PEG (3.346 g, 1.95 mmol, 98%).

$^1$H-NMR ($CDCl_3$) δ=7.80 (2H, d, J=8.4 Hz, 2.6-H of TsO), 7.34 (2H, d, J=8.0 Hz, 3.5-H of Ts), 4.16 (2H, t, J=5.0 Hz, $CH_2$OTs), 3.83~3.45 (~138H, m, $OCH_2$×69), 2.45 (3H, s, 4-$CH_3$ of Ts).

The mono-tosylated PEG (3.346 g, 1.95 mmol) was dissolved in acetonitrile (15 ml), and sodium azide (0.1904 g, 2.93 mmol) was added and refluxed for 32 hours. After completion of the reaction, the solution was cooled to room temperature and water (20 ml) was added. Dichloromethane was added and the organic phase was extracted and dried over anhydrous sodium sulfate. After filtration, the solvent was removed in vacuo to give the mono-azidated PEG (2.889 g, 1.82 mmol, 93%) of a molecular weight of 1540.

$^1$-NMR ($CDCl_3$) δ=3.83~3.45 (~138H, m, $OCH_2$ ×69), 3.39 (2H, t, J=5.0 Hz, $CH_2N_3$).

The mono-azidated PEG (2.889 g, 1.82 mmol) of a molecular weight of 1540 was dissolved in methanol (100 ml), a catalytic amount of platinum dioxide was added and stirred under $H_2$ at room temperature for 2 hours. After completion of the reaction, platinum dioxide was removed on Celite. The solvent was removed in vacuo to give the mono-amino PEG (2.351 g, 1.51 mmol, 83%) of a molecular weight of 1540.

$^1$H-NMR ($CDCl_3$) δ=3.83~3.45 (~138H, m, $OCH_2$×69), 2.86 (2H, t, J=5.2 Hz, $CH_2$N).

3,5-Bis(tetradecyloxy)-4-methoxybenzoic acid (0.173 g, 0.300 mmol) was dissolved in dichloromethane (5 ml), and HOBt (0.0504 g, 0.360 mmol) and EDC.HCl (0.0690 g, 0.360 mmol) were added and stirred at room temperature for one hour. To the dichloromethane solution, a dichloromethane solution (5 ml) of the mono-amino PEG derivative (0.490 g, 0.314 mmol) of a molecular weight of 1540 was added dropwise by use of a dropping funnel and further stirred for one hour. After completion of the reaction, the solution was washed with aqueous 4% $NaHCO_3$ and brine. The organic phase was dried over anhydrous sodium sulfate. After filtration, the solvent was removed in vacuo. The residue was purified by preparatory silica gel thin layer chromatography (chloroform:methanol=9:1) to give a product (0.370 g, 0.175 mmol, 58%) (calculated as a single compound represented by Formula (2)).

$^1$H-NMR ($CDCl_3$) δ=7.04 (2H, s, 2.6-H), 6.97 (1H, br-t, NH), 4.03 (4H, t, J=6.6 Hz, 3.5-$OCH_2$), 3.85 (3H, s, 4-$OCH_3$), 3.71~3.50 (~128H, m, $CH_2OCH_2$), 1.81 (4H, quintet, J=7.6 Hz, 3.5-$OCCH_2$), 1.46 (4H, quintet, J=7.2 Hz, 3.5-$OC_2CH_2$), 1.36~1.22 (40H, m, 3.5-$OC_3C_{10}H_{20}$), 0.88 (6H, t, J=6.8 Hz, 3.5-$OC_{13}CH_3$).

MALDI-TOF/MS measurement of the product was made by using Shimadzu AXIMA CFR plus in the conditions: nitrogen laser (337 nm), reflectron mode, cation detection, cumulated number: 500 times, ionization auxiliary agent: an acetone solution of sodium iodide (1 mg/ml), matrix: dithranol chloroform solution (10 mg/ml), sample concentration: 1 mg/ml (chloroform solution), scan range: m/z 1-5000.

Besides peaks of compounds having an analogous molecular weight distribution to starting PEG of a molecular weight of 1540 corresponding to a compound represented by Formula (2) wherein X=OH, k2=0, m2=29 to 32, n7=2, $R_4=R_6=OC_{14}H_{29}$ and $R_5=OCH_3$, another peaks of compounds having a molecular weight larger by 557 and having a similar molecular weight distribution represented by Formula (1) wherein k1=0, m1=29 to 32, n1=2, $R_1=R_3=OC_{14}H_{29}$ and $R_2=OCH_3$, was detected. Production of the dual-terminal amide derivative was confirmed.

In a lot subjected to analysis, the ratio of peak in height of a uni-terminal amide derivative:a dual-terminal amide derivative was about 5:1.

Example 8

Rheological Measurement of the Composition Obtained by the Same Synthetic Method as in Example 7

The composition obtained by the same synthetic method as in Example 7, was subjected to HPLC analysis (column: DAISO PAK SP-200-5-C4-P, column temperature: 40° C., solvent: an aqueous 70-99% acetonitrile solution, 0.1% TFA, linear concentration gradient, flow rate: 1.0 ml/min). As a result, a composition containing a dual-terminal amide compound corresponding to Formula (1) and a uni-terminal amide compound corresponding to Formula (2) in a ratio of 0.48:1 was obtained. To analyze the sol-gel transition of the composition, the viscoelasticity of aqueous sample solutions was measured. The concentrations of the composition were adjusted to 1 wt %, 2 wt %, 8 wt % and 15 wt %. After sufficiently stirred to give uniform solution, the aqueous sample solutions were stored in a freezer. Measurement was performed by AR-G2 (TA Instruments, Japan). Parallel plates (40 mm) were used and a frequency was set to be 1 Hz. Measurement was performed while raising the temperature of the aqueous sample solutions from 0° C. to 80° C. at a temperature raising rate of 3° C./min. The results are shown in FIG. 7.

It was found that the hydrogelating agent formed hydrogel at a wide concentration range of at least 2 wt % or more and at a wide temperature range. Particularly, the solution was sol state at a concentration of 2 wt % at 37° C., the temperature usually used for animal cell culture, and changed into gel at a temperature of 30° C. or less. The hydrogel has an appropriate temperature property for storing cells.

Example 9

Effect of a Composition Obtained by the Same Synthetic Method as in Example 7 on Storing Hepatic Cells Hepatic cell storage was studied using a lot of the hydrogelating agent obtained in the same synthetic method as in Example 7 and the same lot that was subjected to the rheological measurement in Example 8.

Rat hepatic cells ($6 \times 10^5$ cells) were enclosed in hydrogel prepared to contain a hydrogelating agent at a concentration of 2 w/v % (2 g of the hydrogelating agent in 100 ml of water) together with cell culture medium, placed in an Eppendorf tube and stored in a refrigerator overnight. The next day, the cells were collected, seeded in a 24-well plate and cultured in a medium for hepatic cells. The medium was exchanged every day. After removing the culture supernatant, 1 ml of fresh medium was added and cultured for 3 days. The cells were ultrasonically pulverized and the amount of DNA was measured. As a result, the DNA amount of a control without the agent was 14.7±2.6 μg/ml, whereas the DNA amount of the sample with the hydrogelating agent was 17.4±1.5 μg/ml. Since the DNA amount increases in proportional to the number of cells, it was demonstrated that hydrogel could be used for storing hepatic cells.

Example 10

Effect of a Composition Obtained by the Same Synthetic Method as in Example 7 on Storing Cartilage Cells Cartilage cell storage was studied using a lot of the hydrogelating agent obtained in the same synthetic method as in Example 7 and the same lot that was subjected to the rheological measurement in Example 8.

Rabbit cartilage cells ($1.2 \times 10^6$ cells) were enclosed in hydrogel prepared to contain the hydrogelating agent at a concentration of 2 w/v % together with cell culture medium, placed in an Eppendorf tube and stored in a refrigerator overnight. The next day, the cells were collected, seeded in a 24-well plate and cultured in a medium for cartilage cells. The medium was exchanged at a frequency of twice a week. After removing the culture supernatant by aspiration, 1 ml of fresh medium was added and cultured for 3 weeks. At the final day, the culture solution was removed by aspiration, and the cells were washed with 0.5 ml of PBS (−). The cells were enzymatically decomposed by 1 ml of a protease (bromelain) solution at 60° C. for 30 minutes. The DNA amount of the treated solution was measured. As a result, the DNA amount of a control without the agent was 10.5±0.0 μg/ml, whereas the DNA amount of the sample with the hydrogelating agent was 17.8±1.7 μg/ml. Since the DNA amount increases in proportional to the number of cells, it was demonstrated that hydrogel could be used for storing cartilage cells.

Example 11

Synthesis of a Composition of a Uni-Terminal Amide Compound Represented by Formula (2) Wherein X=OH, k2=0, m2=42 to 45, n2=2, $R_4=R_6=OC_{14}H_{29}$ and $R_4=OCH_3$ and a Dual-Terminal Amide Compound Represented by Formula (1) Wherein k1=0, m1=42 to 45, n1=2, $R_1=R_3=OC_{14}H_{29}$ and $R_2=OCH_3$ PEG (4.00 g, 2.00 mmol) of a molecular weight of 2000 was dissolved in pyridine (10 ml) and p-toluenesulfonyl chloride (0.76 g, 4.00 mmol) was added and stirred at room temperature for 3 hours. After completion of the reaction, chloroform (100 ml) was added and neutralization was performed with 1M HCl (100 ml). The solution was washed with aqueous 4% NaHCO$_3$ and brine. The organic phase was dried over anhydrous sodium sulfate. After filtration, the solvent was removed in vacuo. The residue was purified by silica gel column chromatography (chloroform:methanol=10:1) to give mono-tosylated PEG (4.140 g, 1.92 mmol, 96%) of a molecular weight of 2000.

$^1$H-NMR (CDCl$_3$) δ=7.79 (2H, d, J=8.0 Hz, 2.6-H of TsO), 7.34 (2H, d, J=8.0 Hz, 3.5-H of Ts), 4.16 (2H, t, J=5.2 Hz, CH$_2$OTs), 3.83~3.45 (~178H, m, OCH$_2$×89), 2.45 (3H, s, 4-CH$_3$ of Ts).

The mono-tosylated PEG (4.140 g, 1.92 mmol) was dissolved in acetonitrile (20 ml), and sodium azide (0.195 g, 3.00 mmol) was added and refluxed for 32 hours. After completion of the reaction, the solution was cooled to room temperature and water (20 ml) was added. Dichloromethane was added and the organic phase was extracted and dried over anhydrous sodium sulfate. After filtration, the solvent was removed in vacuo to give mono-azidated PEG (3.280 g, 1.62 mmol, 84%).

$^1$H-NMR (CDCl$_3$) δ=3.83~3.45 (~178H, m, OCH$_2$×89), 3.39 (2H, t, J=5.2 Hz, CH$_2$N$_3$).

The mono-azidated PEG (1.537 g, 0.759 mmol) was dissolved in pyridine (5 ml), and triphenylphosphine (0.394 g, 1.50 mmol) was added and stirred at room temperature for 2 hours. After completion of the reaction, aqueous 28% NH$_4$OH (10 ml) was added and allowed to stand for 2 hours. The solvent was removed in vacuo to give a product mono-amino PEG.

$^1$H-NMR (CDCl$_3$) δ=3.83~3.45 (~178H, m, OCH$_2$×89), 2.86 (2H, t, J=5.2 Hz, CH$_2$N). 3,5-Bis(tetradecyloxy)-4-methoxybenzoic acid (0.202 g, 0.350 mmol) was dissolved in dichloromethane (5 ml), and HOBt (0.060 g, 0.420 mmol) and EDC.HCl (0.081 g, 0.420 mmol) were added and stirred at room temperature for one hour. To the dichloromethane solution, dichloromethane solution (5 ml) of the mono-amino PEG derivative (an excessive amount of unpurified product) was added dropwise by use of a dropping funnel and further stirred for one hour. After completion of the reaction, the solution was washed with aqueous 4% NaHCO$_3$ and brine. The organic phase was dried over anhydrous sodium sulfate. After filtration, the solvent was removed in vacuo. The residue was purified by preparatory silica gel thin layer chromatography (chloroform:methanol=9:1) to give a product (0.439 g, 0.172 mmol, 49%) (calculated as the single compound represented by Formula (2)).

$^1$H-NMR (CDCl$_3$) δ=7.03 (2H, s, 2.6-H), 6.89 (1H, br-t, NH), 4.03 (4H, t, J=6.6 Hz, 3.5-OCH$_2$), 3.85 (3H, s, 4-OCH$_3$), 3.71~3.50 (~180H, m, CH$_2$OCH$_2$), 1.81 (4H, quintet, J=7.2 Hz, 3.5-OCCH$_2$), 1.46 (4H, quintet, J=7.6 Hz, 3.5-OC$_2$H$_2$), 1.36~1.22 (40H, m, 3.5-OC$_3$C$_{10}$H$_{20}$), 0.88 (6H, t, J=6.8 Hz, 3.5-OC$_{13}$CH$_3$).

MALDI-TOF/MS measurement of the product was performed in the same conditions as in Example 7.

Besides peaks of compounds having an analogous molecular weight distribution of starting PEG of a molecular weight of 2000 corresponding to a uni-terminal amide compound represented by Formula (2) wherein X=OH, k2=0, m2=42 to 45, n2=2, R$_4$=R$_6$=OC$_{14}$H$_{29}$ and R$_5$=OCH$_3$, another peaks of compounds having a molecular weight larger by 557 and having a similar molecular weight distribution corresponding to a compound represented by Formula (1), wherein k1=0, m1=42 to 45, n1=2, R$_1$=R$_3$=OC$_{14}$H$_{29}$ and R$_2$=OCH$_3$, were detected. Production of a dual-terminal amide compound was confirmed.

In a lot subjected to analysis, the ratio of peak in height of a uni-terminal amide derivative:a dual-terminal amide derivative was about 4:1.

Example 12

Rheological Measurement of the Composition Obtained by the Same Synthetic Method as in Example 11

The composition obtained by the same synthetic method as in Example 11, was subjected to HPLC analysis (column: DAISO PAK SP-200-5-C4-P, column temperature: 40° C., solvent: an aqueous 70-99% acetonitrile solution, 0.1% TFA, linear concentration gradient, flow rate: 1.0 ml/min). As a result, composition 1 containing a dual-terminal amide compound corresponding to Formula (1) and a uni-terminal amide compound corresponding to Formula (2) in a ratio of 0.16:1 was obtained. To analyze the sol-gel transition of the composition 1, the viscoelasticity of aqueous sample solutions was measured. The concentration of composition 1 was adjusted to 1 wt %, 2 wt %, 8 wt % and 15 wt %. After sufficiently stirred to give uniform solution, the aqueous sample solutions were stored in a freezer. Rheological mesurement was performed in the same manner as in Example 8. The results are shown in FIG. 8.

Similarly, composition 2 was obtained containing a dual-terminal amide compound corresponding to Formula (1) and a uni-terminal amide compound corresponding to Formula (2) in a ratio of 0.45:1. To analyze the sol-gel transition of the composition 2, the viscoelasticity of aqueous sample solutions was measured. The concentration of composition 2 was adjusted to 1 wt %, 2 wt %, 8 wt % and 15 wt %. After sufficiently stirred to give uniform solution, the aqueous sample solutions were stored in a freezer. Rheological measurement was performed in the same manner as in Example 8. The results are shown in FIG. 9.

It was demonstrated that gel transition temperature can be controlled by changing the mixing ratio of a uni-terminal amide derivative and a dual-terminal amide derivative, corresponding to the results of Example 6. Particularly, the gel transition temperature of composition 2 (15 wt% concentration) containing a compound corresponding to Formula (1) and a compound corresponding to Formula (2) in a ratio of 0.45:1 is around 23° C. It was thus demonstrated that composition 2 provides ideal hydrogel for cell culture carrier, which is gel state at 37° C., the temperature usually used for culturing animal cells, and changes into sol state at a low temperature for collecting cells.

Industrial Applicability

The hydrogel provided by the present invention has oligo- or poly(ethylene glycol) moiety, which is known to be biocompatible, and can be used in three-dimensional cell culture, separation/purification of cells and proteins and controlled release of a proteinaceous pharmaceutical product, etc.

The invention claimed is:

1. A process for producing a hydrogel comprising the step of mixing water and benzamide derivative represented by Formula (1):

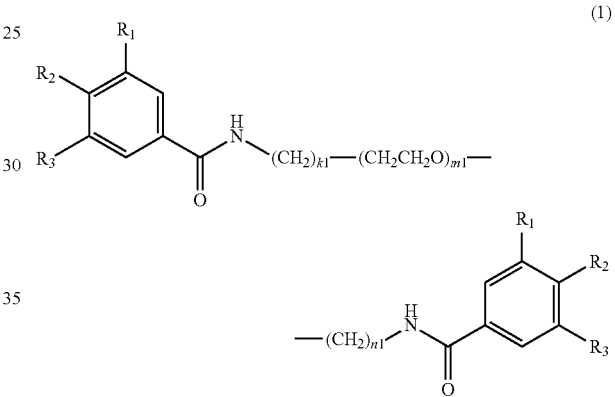

wherein k1 represents an integer of 0 to 4; m1 represents an integer of 1 to 100; and n1 represents an integer of 1 to 6; R$_1$ represents a hydrocarbon group having 8 to 22 carbon atoms in which the hydrocarbon group is bonded to an oxygen atom and the oxygen atom is bonded to the adjacent ring of said derivative; R$_2$ represents H or a hydrocarbon group having 1 to 22 carbon atoms in which the hydrocarbon group is bonded to an oxygen atom and the oxygen atom is bonded to the adjacent ring of said derivative; R$_3$ represents H or a hydrocarbon group having 1 to 22 carbon atoms and a terminal oxygen atom which is bonded to an adjacent phenyl ring; and R$_2$ and R$_3$ are not H at the same time.

2. A hydrogel containing a benzamide derivative represented by Formula (1) and water:

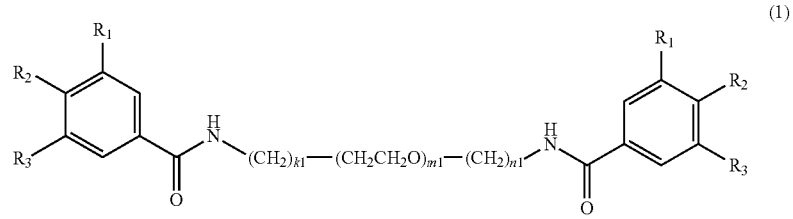

wherein k1 represents an integer of 0 to 4; m1 represents an integer of 1 to 100; and n1 represents an integer of 1 to 6; $R_1$ represents a hydrocarbon group having 8 to 22 carbon atoms in which the hydrocarbon group is bonded to an oxygen atom and the oxygen atom is bonded to the adjacent ring of said derivative; $R_2$ represents H or a hydrocarbon group having 1 to 22 carbon atoms in which the hydrocarbon group is bonded to an oxygen atom and the oxygen atom is bonded to the adjacent ring of said derivative; $R_3$ represents H or a hydrocarbon group having 1 to 22 carbon atoms and a terminal oxygen atom which is bonded to an adjacent phenyl ring; and $R_2$ and $R_3$ are not H at the same time.

3. A process for producing a hydrogel comprising the step of mixing water and a composition containing a benzamide derivative represented by Formula (1) and a benzamide derivative represented by Formula (2);

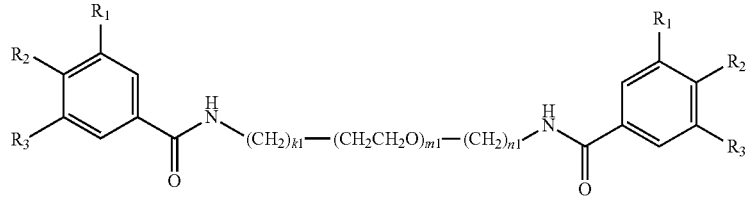

(1)

wherein k1 represents an integer of 0 to 4; m1 represents an integer of 1 to 100; and n1 represents an integer of 1 to 6; $R_1$ represents a hydrocarbon group having 8 to 22 carbon atoms in which the hydrocarbon group is bonded to an oxygen atom and the oxygen atom is bonded to the adjacent ring of said derivative; $R_2$ represents H or a hydrocarbon group having 1 to 22 carbon atoms in which the hydrocarbon group is bonded to an oxygen atom and the oxygen atom is bonded to the adjacent ring of said derivative; $R_3$ represents H or a hydrocarbon group having 1 to 22 carbon atoms in which the hydrocarbon group is bonded to an oxygen atom and the oxygen atom is bonded to the adjacent ring of said derivative; and $R_2$ and $R_3$ are not H at the same time;

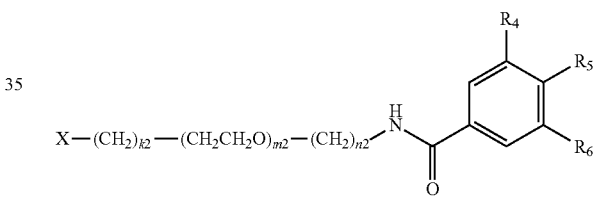

(2)

wherein X represents OH or $NH_2$; k2 represents an integer of 0 to 4; m2 represents an integer of 1 to 100; and n2 represents an integer of 1 to 6; $R_4$ represents a hydrocarbon group having 8 to 22 carbon atoms in which the hydrocarbon group is bonded to an oxygen atom and the oxygen atom is bonded to the adjacent ring of said derivative; $R_5$ represents H or a hydrocarbon group having 1 to 22 carbon atoms in which the hydrocarbon group is bonded to an oxygen atom and the oxygen atom is bonded to the adjacent ring of said derivative; $R_6$ represents H or a hydrocarbon group having 1 to 22 carbon atoms and a terminal oxygen atom which is bonded to an adjacent phenyl ring; and $R_5$ and $R_6$ are not H at the same time.

4. A hydrogel containing a composition containing a benzamide derivative represented by Formula (1) and a benzamide derivative represented by Formula (2) and

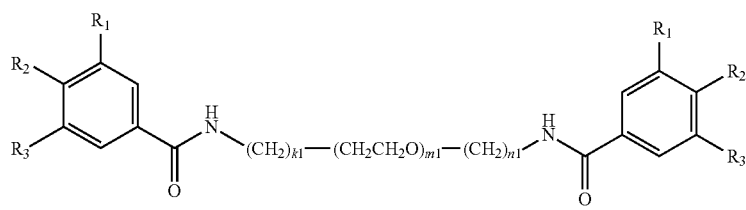

(1)

water;

wherein k1 represents an integer of 0 to 4; m1 represents an integer of 1 to 100; and n1 represents an integer of 1 to 6; $R_1$ represents a hydrocarbon group having 8 to 22 carbon atoms in which the hydrocarbon group is bonded to an oxygen atom and the oxygen atom is bonded to the adjacent ring of said derivative; $R_2$ represents H or a hydrocarbon group having 1 to 22 carbon atoms in which the hydrocarbon group is bonded to an oxygen atom and the oxygen atom is bonded to the adjacent ring of said derivative; $R_3$ represents H or a hydrocarbon group having 1 to 22 carbon atoms in bonded to the adjacent ring of said derivative; and $R_2$ and $R_3$ are not H at the same time;

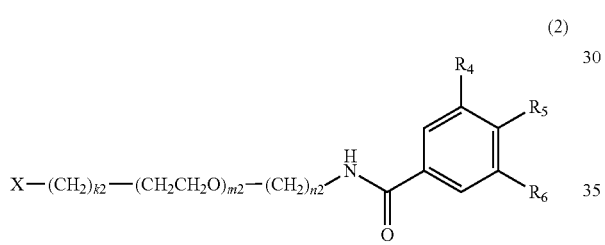

(2)

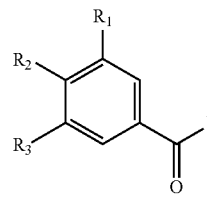

wherein X represents OH or $NH_2$; k2 represents an integer of 0 to 4; m2 represents an integer of 1 to 100; and n2 represents an integer of 1 to 6; $R_4$ represents a hydrocarbon group having 8 to 22 carbon atoms in which the hydrocarbon group is bonded to an oxygen atom and the oxygen atom is bonded to the adjacent ring of said derivative; $R_5$ represents H or a hydrocarbon group having 1 to 22 carbon atoms in which the hydrocarbon group is bonded to an oxygen atom and the oxygen atom is bonded to the adjacent ring of said derivative; $R_6$ represents H or a hydrocarbon group having 1 to 22 carbon atoms in which the hydrocarbon group is bonded to an oxygen atom and the oxygen atom is bonded to the adjacent ring of said derivative; and $R_5$ and $R_6$ are not H at the same time.

5. A benzamide derivative, represented by formula (3):

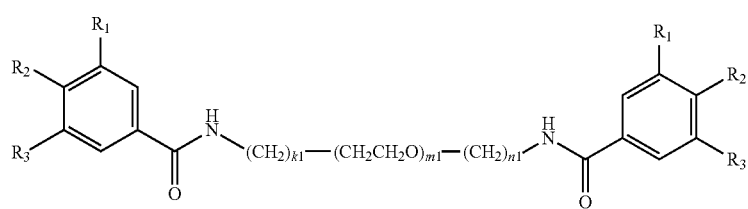

(3)

wherein k1 represents an integer of 0 to 4; m1 represents an integer of 7 to 100; and n1 represents an integer of 2 to 6; $R_1$ and $R_3$ represent a hydrocarbon group having 12 to 18 carbon atoms in which the hydrocarbon group is bonded to an oxygen atom and the oxygen atom is bonded to the adjacent ring of said derivative; and $R_2$ represents H or a hydrocarbon group having 1 to 18 carbon atoms in which the hydrocarbon group is bonded to an oxygen atom and the oxygen atom is bonded to the adjacent ring of said derivative.

6. A process for producing a hydrogel comprising the step of mixing water and the benzamide derivative according to claim 5.

7. A hydrogel, containing the benzamide derivative according to claim 5 and water.

8. A process for producing a hydrogel, comprising the step of mixing water and a composition containing a benzamide derivative represented by Formula (3) and a benzamide derivative represented by Formula (4);

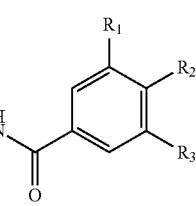

(3)

wherein k1 represents an integer of 0 to 4; m1 represents an integer of 7 to 100; and n1 represents an integer of 2 to 6; $R_1$ and $R_3$ represent a hydrocarbon group having 12 to 18 carbon atoms a terminal oxygen atom which is bonded to an adjacent phenyl ring; and $R_2$ represents H or a hydrocarbon group having 1 to 18 carbon atoms in which the hydrocarbon group is bonded to an oxygen atom and the oxygen atom is bonded to the adjacent ring of said derivative;

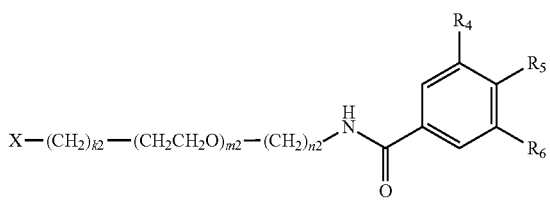

(4)

wherein X represents OH or $NH_2$; k2 represents an integer of 0 to 4; m2 represents an integer of 7 to 100; and n2 represents an integer of 2 to 6; $R_4$ and $R_6$ represent a hydrocarbon group having 12 to 18 carbon atoms in which the hydrocarbon group is bonded to an oxygen atom and the oxygen atom is bonded to the adjacent ring of said derivative; $R_5$ represents H or a hydrocarbon group having 1 to 18 carbon atoms in which the hydrocarbon group is bonded to an oxygen atom and the oxygen atom is bonded to the adjacent ring of said derivative.

9. A hydrogel containing a composition containing a benzamide derivative represented by Formula (3) and a benzamide derivative represented by Formula (4) and water;

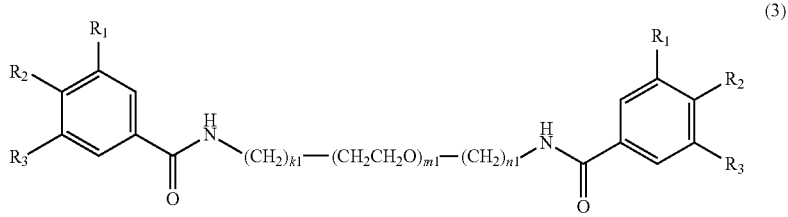

(3)

wherein k1 represents an integer of 0 to 4; m1 represents an integer of 7 to 100; and n1 represents an integer of 2 to 6; $R_1$ and $R_3$ represent a hydrocarbon group having 12 to 18 carbon atoms in which the hydrocarbon group is bonded to an oxygen atom and the oxygen atom is bonded to the adjacent ring of said derivative; and $R_2$ represents H or a hydrocarbon group having 1 to 18 carbon atoms in which the hydrocarbon group is bonded to an oxygen atom and the oxygen atom is bonded to the adjacent ring of said

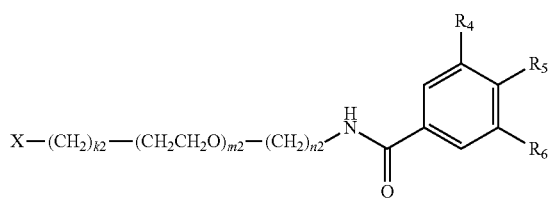

(4)

derivative;

wherein X represents OH or $NH_2$; k2 represents an integer of 0 to 4; m2 represents an integer of 7 to 100; and n2 represents an integer of 2 to 6; $R_4$ and $R_6$ represent a hydrocarbon group having 12 to 18 carbon atoms in which the hydrocarbon group is bonded to an oxygen atom and the oxygen atom is bonded to the adjacent ring of said derivative; $R_5$ represents H or a hydrocarbon group having 1 to 18 carbon atoms in which the hydrocarbon group is bonded to an oxygen atom and the oxygen atom is bonded to the adjacent ring of said derivative.

10. The hydrogel according to claim 2, 4, 7 or 9, having a sol-to-gel transition temperature of 10° C. or more and 40° C. or less associated with temperature rise.

11. A process for producing a hydrogel comprising the step of mixing water and a composition containing a benzamide derivative represented by Formula (5) and a benzamide derivative represented by Formula (6):

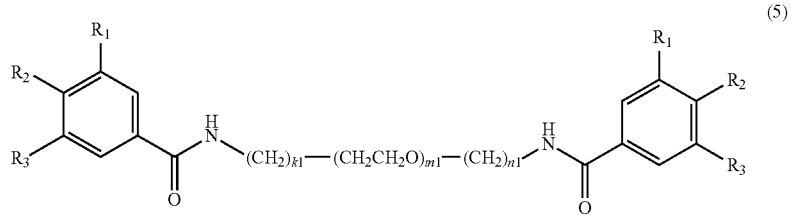

(5)

wherein k1 is 0; m1 is 42 to 45; n1 is 2; $R_1$ is $OC_{14}H_{49}$; $R_2$ is $OCH_3$; and $R_3$ is $OC_{14}H_{49}$;

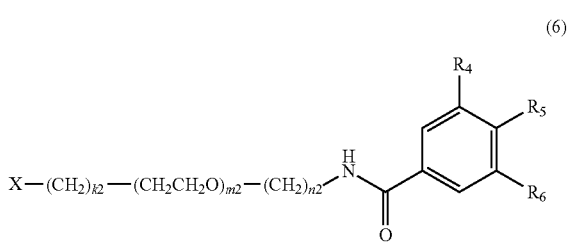

(6)

wherein X is OH; k2 is 0; m2 is 42 to 45; n2 is 2; $R_4$ is $OC_{14}H_{49}$; $R_5$ is $OCH_3$; and $R_6$ is $OC_{14}H_{49}$.

12. A hydrogel comprising a composition containing a benzamide derivative represented by Formula (5) and a benzamide derivative represented by Formula (6) and water, and having a sol-to-gel transition temperature of between 10° C. or more and 40° C.or less associated with temperature rise;

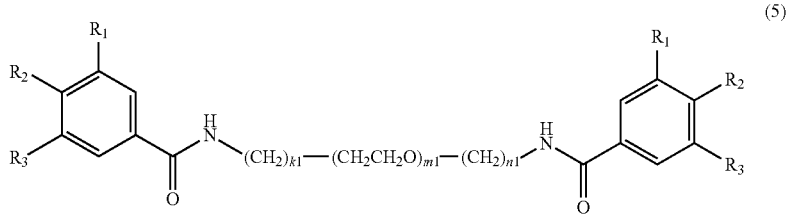
(5)

wherein k1 is 0; m1 is 42 to 45; n1 is 2; $R_1$ is $OC_{14}H_{49}$; $R_2$ is $OCH_3$; and $R_3$ is $OC_{14}H_{49}$;

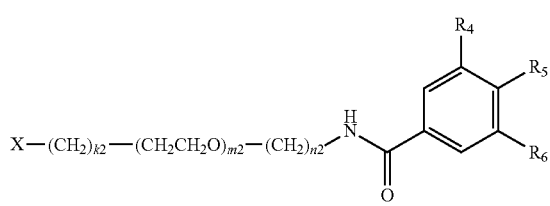
(6)

wherein X is OH; k2 is 0; m2 is 42 to 45; n2 is 2; $R_4$ is $OC_{14}H_{49}$; $R_5$ is $OCH_3$; and $R_6$ is $OC_{14}H_{49}$.

13. The hydrogel according to claim 12, having a sol-to-gel transition temperature of between 20° C. or more and 35° C. or less associated with temperature rise.

14. The hydrogel according to claim 2,4,7 or 9, having a sol-to-gel transition temperature of −5° C. or more and 35° C. or less associated with temperature drop.

15. A process for producing a hydrogel, comprising the step of mixing water and a composition containing a benzamide derivative represented by Formula (7) and a benzamide derivative represented by Formula (8):

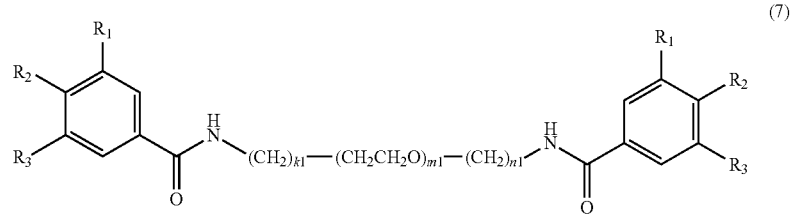
(7)

wherein k1 is 0; m1 is 29 to 32; n1 is 2; $R_1$ is $OC_{14}H_{49}$; $R_2$ is $OCH_3$; and $R_3$ is $OC_{14}H_{49}$;

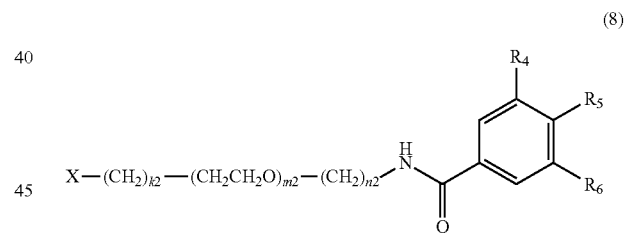
(8)

wherein X is OH; k2 is 0; m2 is 29 to 32; n2 is 2; $R_4$ is $OC_{14}H_{49}$; $R_5$ is $OCH_3$; and $R_6$ is $OC_{14}H_{49}$.

16. A hydrogel, containing a composition containing a benzamide derivative represented by Formula (7) and a benzamide derivative represented by Formula (8) and water, and having a sol-to-gel transition temperature of between −5° C. or more and 35° C. or less associated with temperature drop;

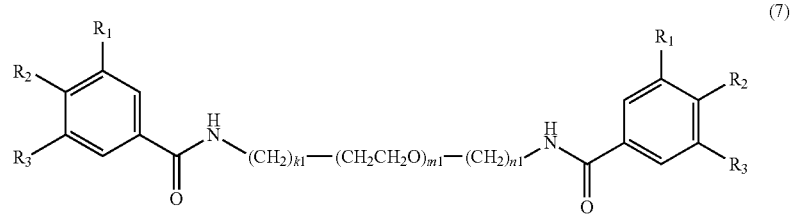
(7)

wherein k1 is 0; m1 is 29 to 32; n1 is 2; $R_1$ is $OC_{14}H_{49}$; $R_2$ is $OCH_3$; and $R_3$ is $OC_{14}H_{49}$;

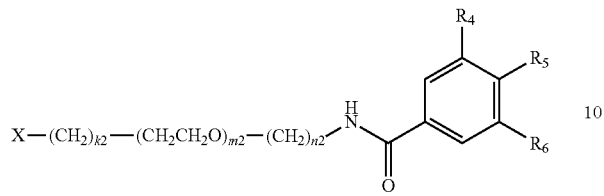

(8)

wherein X is OH; k2 is 0; m2 is 29 to 32; n2 is 2; $R_4$ is $OC_{14}H_{49}$; $R_5$ is $OCH_3$; and $R_6$ is $OC_{14}H_{49}$.

17. The hydrogel according to claim 16, having a sol-to-gel transition temperature of 0° C. or more and 20° C. or less associated with temperature drop.

18. A method for culturing cells which comprises the step of contacting the cells with the hydrogel according to claim 10 and culturing the resultant hydrogel-contacted cells.

19. A method for storing cells which comprises the step of contacting the cells with the hydrogel according to claim 14 and storing the resultant hydrogel-contacted cells.

20. A method for culturing which comprises the step of contacting the cells with the hydrogel according to claim 12 or 13 and culturing the resultant hydrogel-contacted cells.

21. A method for storing cells which comprises the step of contacting the cells with the hydrogel according to claim 16 or 17 and storing the resultant hydrogel-contacted cells.

* * * * *

UNITED STATES PATENT AND TRADEMARK OFFICE
CERTIFICATE OF CORRECTION

Page 1 of 2

PATENT NO. : 8,633,022 B2
APPLICATION NO. : 13/201111
DATED : January 21, 2014
INVENTOR(S) : Hitoshi Tamiaki et al.

It is certified that error appears in the above-identified patent and that said Letters Patent is hereby corrected as shown below:

IN THE SPECIFICATION:

At column 6, lines numbered 35 and 36 (immediately below formula (5)) and line numbered 48 (below formula (6)), in the descriptions of $R_1$, $R_3$, $R_4$ and $R_6$, change "$OC_{14}H_{49}$" to --$OC_{14}H_{29}$--.

At column 7, lines numbered 13 and 14 (immediately below formula (7)) and line numbered 28 (below formula (8)), in the descriptions of $R_1$, $R_3$, $R_4$ and $R_6$, change "$OC_{14}H_{49}$" to --$OC_{14}H_{29}$--.

IN THE CLAIMS:

In claim 11, at column 26, lines numbered 47 and 48 (immediately below formula (5)) and line numbered 62 (below formula (6)), in the descriptions of $R_1$, $R_3$, $R_4$ and $R_6$, change "$OC_{14}H_{49}$" to --$OC_{14}H_{29}$--.

In claim 12, at column 27, lines numbered 12 and 13 (immediately below formula (5)), in the descriptions of $R_1$ and $R_3$, change "$OC_{14}H_{49}$" to --$OC_{14}H_{29}$--.

In claim 12, at column 28, lines numbered 12 and 13 (immediately above claim 13), in the descriptions of $R_4$ and $R_6$, change "$OC_{14}H_{49}$" to --$OC_{14}H_{29}$--.

In claim 15, at column 28, lines numbered 35 and 36 (immediately below formula (7)), in the descriptions of $R_1$ and $R_3$, change "$OC_{14}H_{49}$" to --$OC_{14}H_{29}$--.

In claim 15, at column 28, line numbered 49 (immediately below formula (8)), change "$R_4$ iS" to --$R_4$ is--.

In claim 15, at column 28, line numbered 50 (below formula (8)), in the descriptions of $R_4$ and $R_6$, change "$OC_{14}H_{49}$" to --$OC_{14}H_{29}$--.

Signed and Sealed this
Thirtieth Day of September, 2014

Michelle K. Lee
*Deputy Director of the United States Patent and Trademark Office*

CERTIFICATE OF CORRECTION (continued)
U.S. Pat. No. 8,633,022 B2

IN THE CLAIMS (cont.):

In claim 16, at column 29, lines 1 and 2 and line numbered 16 (below formula (8)), in the descriptions of $R_1$, $R_3$, $R_4$ and $R_6$, change "$OC_{14}H_{49}$" to --$OC_{14}H_{29}$--.